(12) United States Patent
Poznansky et al.

(10) Patent No.: US 6,448,054 B1
(45) Date of Patent: Sep. 10, 2002

(54) PURPOSEFUL MOVEMENT OF HUMAN MIGRATORY CELLS AWAY FROM AN AGENT SOURCE

(75) Inventors: Mark C. Poznansky, Charlestown; Andrew T. Luster, Wellesley; David T. Scadden, Weston, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/546,153

(22) Filed: Apr. 7, 2000

Related U.S. Application Data

(60) Provisional application No. 60/128,272, filed on Apr. 8, 1999, and provisional application No. 60/168,952, filed on Dec. 3, 1999.

(51) Int. Cl.[7] ............................ C12N 9/99; A61K 45/00
(52) U.S. Cl. .................................... 435/184.1; 424/85.1
(58) Field of Search .............................. 424/184.1, 85.1

(56) References Cited

U.S. PATENT DOCUMENTS

| | | |
|---|---|---|
| 5,514,555 A | 5/1996 | Springer et al. ........... 435/7.24 |
| 5,756,084 A | 5/1998 | Honjo et al. ................ 424/85.1 |

FOREIGN PATENT DOCUMENTS

| | | | |
|---|---|---|---|
| WO | WO-9507985 A1 | * | 3/1995 |
| WO | WO-9809642 A2 | * | 3/1998 |

OTHER PUBLICATIONS

Kim et al., Differential chemotactiv behavior of developing T cells in response to thymic chemokines (Jun. 15 1998) Blood, vol. 91, No. 12, pp. 4434–4443.*

Kim et al., CBβ–11/Macrophage inflammatory protein–3β/EBI1–ligand chemokine is an efficacious chemoattractant for T and B cells (1998) vol. 160, pp. 2418–2424.*

Colamarino et al., The axonal chemoattractant netrin–1 is also a chemorepellant for troclear motor axons (May 19 1995) Cell, vol. 81, pp. 621–629.*

Wells et al., Definition, function and pathophysiological significance of chemokine receptors (Sep. 1998) TiPS, vol. 19, pp. 376–380.*

Luster, Chemokines–chemotactic cytokines that mediate inflammation (Feb. 12, 1998) New Englang Journal of Medicine, vol. 338, No. 7, 436–445.*

Baggiolini, Chemokines and leukocyte traffic (Apr. 9, 1998) Nature, vol. 392, pp. 565–568.*

Bailey, et al., "Chemotaxis by Entamoeba Histolytica" *J. Protozool* (1985) 32(2):341–346 Abstract.

Chaffin, K.E. and Perlmutter, R.M. "A Pertussis Toxin–Sensitive Process Controls Thymocyte Emigration" *Eur. J. Immunol.* (1991) 21(10):2565–73 Abstract.

Keating, M.T. and Bonner, J.T. "Negative Chemotaxis in Cellular Slime Molds" *J. Bacteriol.* (1977) 130 (1):144–147 Abstract.

Khan, et al., "Chemotactic Signal Integration in Bacteria" *Proc. Natl. Acad. Sci. USA* (1995) 92(21):9757–9761 Abstract.

Liu, et al., "Analysis of chemokine (S) produced by mouse thymic stromal cell lines" Shih Yen Sheng Wu Hsueh Pao. Mar. 1996; 29(1):25–32. Chinese Abstract.

McFadden, et al., "Rat lymphokines control the migration of nonsensitized lymphocytes", *Cellular Immunology*, 118(2):345–357 (1989) Abstract.

Keller, et al., "Diverging effects of chemo tactic serum peptides and synthetic formylmethionylleucyl phenyl alanine on neutrophil loco motion and adhesion", *Immunology*, 42(3):379–384 (1981) Abstract.

Gebhard, et al., "Inter–alpha–trypsin inhibitor complex component II precursor–human", *PIR Protein Sequence*.

Copy of International Search Report mailed Sep. 13, 2000.

Niggemann, et al., "Locomotory phenotypes of human tumor cell lines and T lymphocytes in a three–dimensional collagen lattice." *Cancer Lett.*, Oct. 14;118(2):173–80 (1997).

Berman, et al., "Functional characteristics of histamine receptor–bearing mononuclear cells. II. Identification and characterization of two histamine–induced human lymphokines that inhibit lymphocyte migration." *J. Immunol.*, Sep;133(3):1495–504 (1984).

* cited by examiner

*Primary Examiner*—Jon P. Weber
(74) *Attorney, Agent, or Firm*—Wolf, Greenfield and Sacks, P.C.

(57) ABSTRACT

This invention relates to methods and compositions for modulating movement of eukaryotic cells with migratory capacity. More specifically, the invention relates to methods and compositions for modulating movement of cells of hematopoietic, neural, epithelial, or mesenchymal origin, in a specific site in a subject. The foregoing are useful, inter alia, in the treatment of conditions characterized by a need to modulate migratory-cell movement associated with specific sites in a subject. More specifically, specific sites include sites of inflammation and modulation of migratory-cell movement is movement away from an agent source, or repulsion. Other sites include tumor sites, sites of pathogenic infection, and germ cell bearing sites.

11 Claims, 10 Drawing Sheets

SEQUENCE LISTING

<160> NUMBER OF SEQ ID NOS: 1

<210> SEQ ID NO 1
<211> LENGTH: 946
<212> TYPE: PRT
<213> ORGANISM: Homo Sapiens

<400> SEQUENCE: 1

```
Met Lys Arg Leu Thr Cys Phe Phe Ile Cys Phe Phe Leu Ser Glu Val
1               5                   10                  15

Ser Gly Phe Glu Ile Pro Ile Asn Gly Leu Ser Glu Phe Val Asp Tyr
            20                  25                  30

Glu Asp Leu Val Glu Leu Ala Pro Gly Lys Phe Gln Leu Val Ala Glu
        35                  40                  45
```

```
Asn Arg Arg Tyr Gln Arg Ser Leu Pro Gly Glu Ser Glu Met Met
 50                  55                  60

Glu Glu Val Asp Gln Val Thr Leu Tyr Ser Tyr Lys Val Gln Ser Thr
 65                  70                  75                  80

Ile Thr Ser Arg Met Ala Thr Thr Met Ile Gln Ser Lys Val Val Asn
                 85                  90                  95

Asn Ser Pro Gln Pro Gln Asn Val Val Phe Asp Val Gln Ile Pro Lys
                100                 105                 110

Gly Ala Phe Ile Ser Asn Phe Ser Met Thr Val Asp Gly Lys Thr Phe
                115                 120                 125

Arg Ser Ser Ile Lys Glu Lys Thr Val Gly Arg Ala Leu Tyr Ala Gln
130                 135                 140

Ala Arg Ala Lys Gly Lys Thr Ala Gly Leu Val Arg Ser Ser Ala Leu
145                 150                 155                 160

Asp Met Glu Asn Phe Arg Thr Glu Val Asn Val Leu Pro Gly Ala Lys
                165                 170                 175

Val Gln Phe Glu Leu His Tyr Gln Glu Val Lys Trp Arg Lys Leu Gly
                180                 185                 190

Ser Tyr Glu His Arg Ile Tyr Leu Gln Pro Gly Arg Leu Ala Lys His
                195                 200                 205

Leu Glu Val Asp Val Trp Val Ile Glu Pro Gln Gly Leu Arg Phe Leu
210                 215                 220

His Val Pro Asp Thr Phe Glu Gly His Phe Asp Gly Val Pro Val Ile
225                 230                 235                 240

Ser Lys Gly Gln Gln Lys Ala His Val Ser Phe Lys Pro Thr Val Ala
                245                 250                 255

Gln Gln Arg Ile Cys Pro Ser Cys Arg Glu Thr Ala Val Asp Gly Glu
                260                 265                 270

Leu Val Val Leu Tyr Asp Val Lys Arg Glu Lys Ala Gly Glu Leu
                275                 280                 285

Glu Val Phe Asn Gly Tyr Phe Val His Phe Ala Pro Asp Asn Leu
290                 295                 300

Asp Pro Ile Pro Lys Asn Ile Leu Phe Val Ile Asp Val Ser Gly Ser
305                 310                 315                 320

Met Trp Gly Val Lys Met Lys Gln Thr Val Glu Ala Met Lys Thr Ile
                325                 330                 335

Leu Asp Asp Leu Arg Ala Glu Asp His Phe Ser Val Ile Asp Phe Asn
                340                 345                 350

Gln Asn Ile Arg Thr Trp Arg Asn Asp Leu Ile Ser Ala Thr Lys Thr
                355                 360                 365

Gln Val Ala Asp Ala Lys Arg Tyr Ile Glu Lys Ile Gln Pro Ser Gly
370                 375                 380

Gly Thr Asn Ile Asn Glu Ala Leu Leu Arg Ala Ile Phe Ile Leu Asn
385                 390                 395                 400

Glu Ala Asn Asn Leu Gly Leu Leu Asp Pro Asn Ser Val Ser Leu Ile
                405                 410                 415

Ile Leu Val Ser Asp Gly Asp Pro Thr Val Gly Glu Leu Lys Leu Ser
                420                 425                 430

Lys Ile Gln Lys Asn Val Lys Glu Asn Ile Gln Asp Asn Ile Ser Leu
                435                 440                 445

Phe Ser Leu Gly Met Gly Phe Asp Val Asp Tyr Asp Phe Leu Lys Arg
                450                 455                 460

Leu Ser Asn Glu Asn His Gly Ile Ala Gln Arg Ile Tyr Gly Asn Gln
```

-continued

```
465                 470                 475                 480
Asp Thr Ser Ser Gln Leu Lys Lys Phe Tyr Asn Gln Val Ser Thr Pro
                485                 490                 495
Leu Leu Arg Asn Val Gln Phe Asn Tyr Pro His Thr Ser Val Thr Asp
                500                 505                 510
Val Thr Gln Asn Asn Phe His Asn Tyr Phe Gly Gly Ser Glu Ile Val
                515                 520                 525
Val Ala Gly Lys Phe Asp Pro Ala Lys Leu Asp Gln Ile Glu Ser Val
            530                 535                 540
Ile Thr Ala Thr Ser Ala Asn Thr Gln Leu Val Leu Glu Thr Leu Ala
545                 550                 555                 560
Gln Met Asp Asp Leu Gln Asp Phe Leu Ser Lys Asp Lys His Ala Asp
                565                 570                 575
Pro Asp Phe Thr Arg Lys Leu Trp Ala Tyr Leu Thr Ile Asn Gln Leu
                580                 585                 590
Leu Ala Glu Arg Ser Leu Ala Pro Thr Ala Ala Lys Arg Arg Ile
                595                 600                 605
Thr Arg Ser Ile Leu Gln Met Ser Leu Asp His His Ile Val Thr Pro
            610                 615                 620
Leu Thr Ser Leu Val Ile Glu Asn Glu Ala Gly Asp Glu Arg Met Leu
625                 630                 635                 640
Ala Asp Ala Pro Pro Gln Asp Pro Ser Cys Cys Ser Gly Ala Leu Tyr
                645                 650                 655
Tyr Gly Ser Lys Val Val Pro Asp Ser Thr Pro Ser Trp Ala Asn Pro
                660                 665                 670
Ser Pro Thr Pro Val Ile Ser Met Leu Ala Gln Gly Ser Gln Val Leu
                675                 680                 685
Glu Ser Thr Pro Pro His Val Met Arg Val Glu Asn Asp Pro His
            690                 695                 700
Phe Ile Ile Tyr Leu Pro Lys Ser Gln Lys Asn Ile Cys Phe Asn Ile
705                 710                 715                 720
Asp Ser Glu Pro Gly Lys Ile Leu Asn Leu Val Ser Asp Pro Glu Ser
                725                 730                 735
Gly Ile Val Val Asn Gly Gln Leu Val Gly Ala Lys Lys Pro Asn Asn
                740                 745                 750
Gly Lys Leu Ser Thr Tyr Phe Gly Lys Leu Gly Phe Tyr Phe Gln Ser
            755                 760                 765
Glu Asp Ile Lys Ile Glu Ile Ser Thr Glu Thr Ile Thr Leu Ser His
            770                 775                 780
Gly Ser Ser Thr Phe Ser Leu Ser Trp Ser Asp Thr Ala Gln Val Thr
785                 790                 795                 800
Asn Gln Arg Val Gln Ile Ser Val Lys Lys Glu Lys Val Val Thr Ile
                805                 810                 815
Thr Leu Asp Lys Glu Met Ser Phe Ser Val Leu Leu His Arg Val Trp
                820                 825                 830
Lys Lys His Pro Val Asn Val Asp Phe Leu Gly Ile Tyr Ile Pro Pro
                835                 840                 845
Thr Asn Lys Phe Ser Pro Lys Ala His Gly Leu Ile Gly Gln Phe Met
                850                 855                 860
Gln Glu Pro Lys Ile His Ile Phe Asn Glu Arg Pro Gly Lys Asp Pro
865                 870                 875                 880
Glu Lys Pro Glu Ala Ser Met Glu Val Lys Gly Gln Lys Leu Ile Ile
                885                 890                 895
```

```
-continued

Thr Arg Gly Leu Gln Lys Asp Tyr Arg Thr Asp Leu Val Phe Gly Thr
            900                 905                 910

Asp Val Thr Cys Trp Phe Val His Asn Ser Gly Lys Gly Phe Ile Asp
        915                 920                 925

Gly His Tyr Lys Asp Tyr Phe Val Pro Gln Leu Tyr Ser Phe Leu Lys
    930                 935                 940

Arg Pro
945
```

PURPOSEFUL MOVEMENT OF HUMAN MIGRATORY CELLS AWAY FROM AN AGENT SOURCE

RELATED APPLICATIONS

This application claims priority under 35 U.S.C. §119(e) from Provisional U.S. Patent Application Ser. No. 60/128,272 filed on Apr. 8, 1999, and Provisional U.S. Patent Application Ser. No. 60/168,952 filed on Dec. 3, 1999, both entitled PURPOSEFUL MOVEMENT OF HUMAN MIGRATORY CELLS AWAY FROM AN AGENT SOURCE. The contents of the provisional applications are hereby expressly incorporated by reference.

GOVERNMENT SUPPORT

This work was funded in part by grant number NHLBI-44851 from the National Institutes of Health. Accordingly, the United States Government may have certain rights to this invention.

FIELD OF THE INVENTION

This invention relates to methods and compositions for modulating movement of eukaryotic cells with migratory capacity. More specifically, the invention relates to methods and compositions for modulating movement of cells of hematopoietic, neural, epithelial, or mesenchymal origin, in a specific site in a subject. The foregoing are useful, inter alia, in the treatment of conditions characterized by a need to modulate migratory-cell movement associated with specific sites in a subject. Specific sites include sites of inflammation and modulation of migratory-cell movement is movement away from an agent source, or repulsion.

BACKGROUND OF THE INVENTION

Cell movement in response to specific stimuli is observed to occur in prokaryotes and eukaryotes (Doetsch R N and Seymour W F., 1970; Bailey G B et al., 1985). Cell movement seen in these organisms has been classified into three types; chemotaxis or the movement of cells along a gradient towards an increasing concentration of a chemical; negative chemotaxis which has been defined as the movement down a gradient of a chemical stimulus and chemokinesis or the increased random movement of cells induced by a chemical agent. The receptors and signal transduction pathways for the actions of specific chemotactically active compounds have been extensively defined in prokaryotic cells. Study of *E. Coli* chemotaxis has revealed that a chemical which attracts the bacteria at some concentrations and conditions may also act as a negative chemotactic chemical or chemorepellent at others (Tsang N et al., 1973; Repaske D) and Adler J. 1981; Tisa L S and Adler J., 1995; Taylor B L and Johnson M S., 1998).

Chemotaxis and chemokinesis have been observed to occur in mammalian cells (McCutcheon M W, Wartman W and H M Dixon, 1934; Lotz M and H Harris 1956; Boyden S V 1962) in response to the class of proteins, called chemokines (Ward S G and Westwick J; 1998; Kim C H et al., 1998; Baggiolini M, 1998; Farber J M; 1997).

Chemokines induce cell locomotion by signaling through G-protein coupled receptors (Wells T N et al., 1998). The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant, cytomegalovirus receptors, etc.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction. Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy-terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise a hydrophilic socket formed by several G-protein coupled receptors transmembrane domains, which socket is surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as including the TM3 aspartate residue. Additionally, TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., *Endoc Rev*, 1989, 10:317–331). Different G-protein a-subunits preferentially stimulate particular effectors to modulate various biological functions in a cell. Phosphorylation of cytoplasmic residues of G-protein coupled receptors have been identified as an important mechanism for the regulation of G-protein coupling of some G-protein coupled receptors. G-protein coupled receptors are found in numerous sites within a mammalian host. Chemokine-induced cell chemotaxis and chemokinesis are thought to be mediated via a $G_{\alpha i}$-linked signal transduction pathway and can be blocked by pertussis toxin (PTX) (Luster A D, 1998; Baggiolini, 1998).

The chemokine, SDF-1α, causes immigration of subpopulations of leukocytes into sites of inflammation (Aiuti A et al. 1997; Bleul C C et al. 1996; Bleul C C et al., 1996; Oberlin E et al., 1996). Furthermore, mice engineered to be deficient in SDF-1α or its receptor, CXCR-4, have abnormal development of hematopoietic tissues and B-cells manifesting a failure of fetal liver stem cells to migrate to bone marrow (Friedland J S, 1995; Tan J and Thestrup-Pedersen K, 1995; Corrigan C J and Kay A B, 1996; Qing M, et al, 1998; Ward S G et al. 1998).

Although chemotaxis and chemokinesis have been defined in cell subpopulations in mammals, negative chemotaxis of peripheral blood cells from mammals has only been observed in response to non-specific stimuli such as cell lysates or tumor tissue fragments (Jochims, 1927; McCutcheon et al. 1939; Bessis M and Burte B., 1965; Noble and Bentley, 1981) and reports have been very limited. The precise mechanism of negative chemotaxis in higher eukaryotic cell subpopulations, including the definition of specific stimuli and signal transduction pathways of negative chemotaxis has not been defined. Furthermore, although chemoattractants had been shown to serve as repellents in prokaryotic systems, no analogous system of a dual action chemoattractant/chemorepellent compound has been identified in higher eukaryotes.

SUMMARY OF THE INVENTION

We describe herein the isolation of agents with migratory-cell repellant activity (hereinafter "fugetactic agents" and "fugetactic activity," and/or "chemo-fugetaxis"). We also describe the identification of previously isolated agents as fugetactic agents at defined concentrations. The invention provides pharmaceutical compositions containing the foregoing fugetactic agents, and various therapeutic and diagnostic methods utilizing the foregoing fugetactic agents. The invention also provides isolated fugetactic polypeptides and agents which bind such polypeptides, including antibodies. The foregoing can be used, inter alia, in the treatment of conditions characterized by a need to modulate migratory-cell movement in specific sites in a subject. Important such sites include inflammation sites. The invention also provides methods for identifying agents useful in the modulation of such fugetactic activity.

According to one aspect of the invention, a thymic stromal-cell isolate is provided that repels immune cells when contacted with immune cells, and does not contain an immune cell repelling concentration of SDF-1α. In certain embodiments, the immune cells that are repelled by the thymic stromal-cell isolate are mature T-cells. In some embodiments, the thymic stromal-cell isolate comprises a polypeptide, and it is the polypeptide that repels the immune cells. In certain embodiments, the thymic stromal-cell isolate mediates its repellant effects through a G-protein transduction pathway. In further embodiments, the thymic stromal-cell isolate is a supernatant, or fraction thereof, of thymic stromal-cells. In yet further embodiments, the thymic stromal-cell isolate is a substantially pure polypeptide. In some embodiments, the polypeptide is not genistein inhibited, and/or is wortmannin inhibited.

According to another aspect of the invention, a substantially pure organic agent that repels mature T-cells at effective concentrations but not at concentrations lower than effective concentrations, is provided. The agent is present at effective concentrations in the supernatant of confluent thymic stromal-cells, cultured under standard conditions for a period of at least one hour, and the culture conditions include a ratio of $10^7$ cells/10 ml medium. The agent is also heat sensitive, protease sensitive, and it elutes-off an ion exchange column with 0.5M NaCl at pH 6.3, and is not SDF-1α. In an important embodiment, the agent is a polypeptide.

According to a further aspect of the invention, a pharmaceutical composition is provided. The pharmaceutical composition includes a thymic stromal-cell isolate according to any of the foregoing embodiments, in a pharmaceutically effective amount to repel immune cells, and a pharmaceutically acceptable carrier.

In a further aspect, the invention provides another pharmaceutical composition. The pharmaceutical composition includes a substantially pure organic agent that repels mature T-cells at effective concentrations but not at concentrations lower than effective concentrations, according to any of the foregoing embodiments, in a pharmaceutically effective amount to repel mature T-cells, and a pharmaceutically acceptable carrier. In some embodiments, the agent is not SDF-1α. In an important embodiment, the agent is a polypeptide.

According to another aspect of the invention, an isolated binding polypeptide which binds selectively to a thymic stromal-cell isolate or agent in the isolate with fugetactic activity according to any of the foregoing embodiments, is also provided. In certain embodiments, the isolated binding polypeptide is an antibody or an antibody fragment such as a Fab fragment, a F(ab)$_2$ fragment, or a fragment including a CDR3 region selective for the thymic stromal-cell isolate or agent in the isolate with fugetactic activity.

According to a further aspect, the invention provides another isolated binding polypeptide which binds selectively to a substantially pure organic agent that repels mature T-cells according to any of the foregoing embodiments. In certain embodiments, the isolated binding polypeptide is an antibody or an antibody fragment such as a Fab fragment, a F(ab)$_2$ fragment, or a fragment including a CDR3 region selective for the thymic stromal-cell isolate or agent in the isolate with fugetactic activity.

According to another aspect of the invention, another pharmaceutical composition is provided. This pharmaceutical composition includes an isolated binding polypeptide according to any of the foregoing embodiments which binds selectively to: (i) a thymic stromal-cell isolate, or (ii) a substantially pure organic agent that repels mature T-cells, or (iii) SDF-1α, (according to any of the foregoing embodiments), in a pharmaceutically effective amount to inhibit repulsion of immune cells and/or T cells by the thymic stromal-cell isolate, the substantially pure organic agent that repels mature T-cells, and/or SDF-1α, respectively, and a pharmaceutically acceptable carrier.

According to the invention a method for isolating a stromal-cell derived fugetactic agent is provided. The method involves preparing a culture of stromal-cells, isolating a supernatant suspected of containing a fugetactic agent from the culture of stromal-cells, fractionating the supernatant into a plurality of fractions, contacting a fraction from the plurality of fractions with a cell with migratory capacity, measuring movement of the cell with migratory capacity and determining whether the movement of the cell with migratory capacity is movement away from the fraction, wherein movement of the cell with migratory capacity away from the fraction is indicative of the presence of a fugetactic agent in the fraction. In certain embodiments, the stromal-cells are thymic stromal-cells and the cell with migratory capacity is a hematopoietic cell.

In certain embodiments, the stromal-cells are isolated from an immune-privileged site/tissue. In preferred embodiments, the cell with migratory capacity is a hematopoietic cell.

In any of the foregoing embodiments, the fraction from the plurality of fractions is undiluted or concentrated.

According to another aspect of the invention, a method of inhibiting migration of immune cells to a specific site in a subject is provided. The method involves locally administering to a specific site in a subject in need of such treatment a fugetactic agent in an amount effective to inhibit migration of immune cells to the specific site in a subject. In certain embodiments the specific site is a site of inflammation. In other embodiments, when the specific site is the site of inflammation, the method further comprises co-administering a non-fugetactic agent that inhibits migration of immune cells to the site of inflammation in the subject. In certain embodiments, the non-fugetactic agent includes an anti-inflammatory agent and/or an immunosuppressant.

In certain embodiments, the subject has an autoimmune disease. In preferred embodiments, the autoimmune disease includes rheumatoid arthritis, uveitis, insulin-dependent diabetes mellitus, hemolytic anemias, rheumatic fever, Crohn's disease, Guillain-Barre syndrome, psoriasis, thyroiditis, Graves' disease, myasthenia gravis, glomerulonephritis, autoimmune hepatitis, systemic lupus erythematosus. In further embodiments, the subject has multiple sclerosis, an abscess, a transplant, an implant, atherosclerosis, and/or myocarditis.

In any of the foregoing aspects and embodiments of the invention, the fugetactic agent is a CXCR-4 ligand. In certain embodiments, CXCR-4 ligands include, but are not limited to, HIV-1$_{IIIB}$ gp120, small molecules T134 and MD3010, and/or T22 ([Tyr5,12,Lys7]-polyphemusin II). In some embodiments, the fugetactic agent is SDF-1α at a concentration higher than about 1 μg/ml, HIV-1$_{IIIB}$ gp120 at a concentration higher than about 200 ng/ml, non-diluted thymic stromal-cell-derived medium, concentrated thymic stromal-cell-derived medium, or thymic stromal-cell-derived polypeptide factor. In certain embodiments, the thymic stromal-cell-derived polypeptide factor mediates its chemorepellant effects through a G-protein transduction pathway. In other embodiments, the thymic stromal-cell-derived polypeptide factor is not genistein inhibited. In further embodiments, the thymic stromal-cell-derived polypeptide factor is wortmannin inhibited.

According to one aspect of the invention, a HepG2-cell isolate is provided that repels immune cells when contacted with immune cells. HepG2 is a cell line derived from human hepatocarcinoma (liver cancer). In certain embodiments, the immune cells that are repelled by the HepG2-cell isolate are mature T-cells. In some embodiments, the HepG2-cell isolate is a supernatant, or fraction thereof, of HepG2 cells. In further embodiments, the HepG2-cell isolate comprises a polypeptide, and it is the polypeptide that repels the immune cells. In yet further embodiments, the HepG2-cell isolate is a substantially pure polypeptide. A preferred such substantially pure polypeptide present in a HepG2-cell isolate is the polypeptide previously identified as inter-α-trypsin inhibitor heavy-chain II precursor (ITI H2) (SEQ ID NO: 1, GenBank Acc. No. P19823), or fragments thereof. In further embodiments, the substantially pure polypeptide present in a HepG2-cell isolate is the polypeptide having an amino acid sequence according to any one of GenBank Acc. Nos.: IYHU2, NP_034712, NP_002207, Q61703, P97279, 002668, CAA72308 (Y11545), BAA13939 (D89286), S54354, CAA49842(X70392), AAA60558(M18193), CAA30160(X07173), 1409219A, or AAA59195(M33033) (all members of the ITI H2 family of polypeptides), or fragments thereof.

According to another aspect of the invention, a substantially pure organic agent that repels mature T-cells at effective concentrations but not at concentrations lower than effective concentrations, is provided. The agent is present at effective concentrations in the supernatant of confluent HepG2 cells, cultured under standard conditions for a period of at least one hour, and the culture conditions include a ratio of $10^7$ cells/10 ml medium. The agent is also heat sensitive, protease sensitive, and it elutes-off an ion exchange heparin column with 0.3M NaCl at pH 7.0. In an important embodiment, the agent is a polypeptide. In one embodiment, the polypeptide has a molecular weight of about 110 kD on a silver-stained SDS-PAGE gel. A preferred polypeptide is the polypeptide previously identified as inter-α-trypsin inhibitor heavy-chain II precursor (ITI H2) (SEQ ID NO: 1, GenBank Acc. No. P19823), or fragments thereof.

According to a further aspect of the invention, a pharmaceutical composition is provided. The pharmaceutical composition includes a HepG2-cell isolate according to any of the foregoing embodiments, in a pharmaceutically effective amount to repel immune cells, and a pharmaceutically acceptable carrier.

In a further aspect, the invention provides another pharmaceutical composition. The pharmaceutical composition includes a substantially pure organic agent that repels mature T-cells at effective concentrations but not at concentrations lower than effective concentrations, according to any of the foregoing embodiments relating to HepG2-cell isolates, in a pharmaceutically effective amount to repel mature T-cells, and a pharmaceutically acceptable carrier. In an important embodiment, the agent is a polypeptide.

According to another aspect of the invention, an isolated binding polypeptide which binds selectively to a HepG2-cell isolate or agent in the HepG2-cell isolate with fugetactic activity according to any of the foregoing embodiments, is also provided. In certain embodiments, the isolated binding polypeptide is an antibody or an antibody fragment such as a Fab fragment, a F(ab)$_2$ fragment, or a fragment including a CDR3region selective for the HepG2-cell isolate or agent in the HepG2-cell isolate with fugetactic activity.

According to a further aspect, the invention provides another isolated binding polypeptide which binds selectively to a substantially pure organic agent that repels mature T-cells according to any of the foregoing embodiments relating to HepG2-cell isolates. In certain embodiments, the isolated binding polypeptide is an antibody or an antibody fragment such as a Fab fragment, a F(ab)$_2$ fragment, or a fragment including a CDR3region selective for the HepG2-cell isolate or agent in the HepG2-cell isolate with fugetactic activity.

According to another aspect of the invention, another pharmaceutical composition is provided. This pharmaceutical composition includes an isolated binding polypeptide according to any of the foregoing embodiments which binds selectively to a HepG2-cell isolate (according to any of the foregoing embodiments), in a pharmaceutically effective amount to inhibit repulsion of immune cells and/or T cells by the HepG2-cell isolate, and a pharmaceutically acceptable carrier.

According to one aspect of the invention, a Kaposi's Sarcoma Herpes Virus (KSHV) infected-cell isolate is provided that repels immune cells when contacted with immune cells. In certain embodiments, the immune cells that are repelled by the KSHV infected-cell isolate are mature T-cells. In some embodiments, the KSHV infected-cell isolate is a supernatant, or fraction thereof, of KSHV infected-cells, preferably of chronically infected KSHV cells. Preferred chronically infected KSHV cells are cell lines BCBL-1 and VG-1. In further embodiments, the KSHV infected-cell isolate comprises a polypeptide, and it is the polypeptide that repels the immune cells. In yet further embodiments, the KSHV infected-cell isolate is a substantially pure polypeptide.

According to another aspect of the invention, a substantially pure organic agent that repels mature T-cells at effective concentrations but not at concentrations lower than effective concentrations, is provided. The agent is present at effective concentrations in the supernatant of confluent KSHV infected-cells, cultured under standard conditions for a period of at least one hour, and the culture conditions include a ratio of $10^7$ cells/10 ml medium. The agent is also heat sensitive, and/or protease sensitive. In an important embodiment, the agent is a polypeptide.

According to a further aspect of the invention, a pharmaceutical composition is provided. The pharmaceutical composition includes a KSHV infected-cell isolate according to any of the foregoing embodiments, in a pharmaceutically effective amount to repel immune cells, and a pharmaceutically acceptable carrier.

In a further aspect, the invention provides another pharmaceutical composition. The pharmaceutical composition includes a substantially pure organic agent that repels mature T-cells at effective concentrations but not at concentrations lower than effective concentrations, according to any of the foregoing embodiments relating to KSHV infected-cell isolates, in a pharmaceutically effective amount to repel mature T-cells, and a pharmaceutically acceptable carrier. In an important embodiment, the agent is a polypeptide.

According to another aspect of the invention, an isolated binding polypeptide which binds selectively to a KSHV infected-cell isolate or agent in the KSHV infected-cell isolate with fugetactic activity according to any of the foregoing embodiments, is also provided. In certain embodiments, the isolated binding polypeptide is an antibody or an antibody fragment such as a Fab fragment, a F(ab)$_2$ fragment, or a fragment including a CDR3 region selective for the KSHV infected-cell isolate or agent in the KSHV infected-cell isolate with fugetactic activity.

According to a further aspect, the invention provides another isolated binding polypeptide which binds selectively to a substantially pure organic agent that repels mature T-cells according to any of the foregoing embodiments relating to KSHV infected-cell isolates. In certain embodiments, the isolated binding polypeptide is an antibody or an antibody fragment such as a Fab fragment, a F(ab)$_2$ fragment, or a fragment including a CDR3 region selective for the KSHV infected-cell isolate or agent in the KSHV infected-cell isolate with fugetactic activity.

According to another aspect of the invention, another pharmaceutical composition is provided. This pharmaceutical composition includes an isolated binding polypeptide according to any of the foregoing embodiments which binds selectively to a KSHV infected-cell isolate (according to any of the foregoing embodiments), in a pharmaceutically effective amount to inhibit repulsion of immune cells and/or T cells by the KSHV infected-cell isolate, and a pharmaceutically acceptable carrier.

According to another aspect of the invention, a method for promoting migration of cells away from a specific site in a subject is provided. The method involves locally-administering to a specific site in a subject in need of such treatment a fugetactic agent in an amount effective to promote migration of cells away from the specific site in the subject. In some embodiments. the specific site is an inflammation site. In certain embodiments, the specific site is a germ cell-containing site. In further embodiments, the specific site is an area surrounding a tumor, but not the immediate area surrounding the tumor. In some important embodiments, the specific site is a transplanted tissue and/or an implant. Important fugetactic agents, cell-types, and so on, are as described above. In any of the foregoing embodiments, preferred cells are immune cells.

According to a further aspect of the invention, a method for distinguishing mature T-cells from immature T-cells in vitro is provided. The method involves contacting a fugetactic agent with a mixed population of mature and immature T-cells and measuring cell movement relative to the fugetactic agent, wherein movement of cells away from the fugetactic agent is indicative of mature T-cells.

According to another aspect of the invention, a method of screening for fugetactic agents is provided. The method involves contacting an agent suspected of being a fugetactic agent with a cell with migratory capacity, measuring movement of the cell with migratory capacity relative to the agent, and determining whether the movement of the cell with migratory capacity is movement away from the agent, wherein movement of the cell with migratory capacity away from the agent is indicative of the agent being a fugetactic agent. In certain embodiments, the cell with migratory capacity is a hematopoietic cell. In some embodiments, the cell with migratory capacity is a neural cell. In further embodiments, the cell with migratory capacity is an epithelial cell. In yet further embodiments, the cell with migratory capacity is a mesenchymal cell. In some embodiments, the cell with migratory capacity is an embryonic stem cell. In certain embodiments, the cell with migratory capacity is a germ cell. In another embodiment, the agent depicted of being a fugetactic agent is known to be a chemoattractant at a defined concentration and a fugetactic agent at a concentration higher than the defined concentration. In preferred embodiments such fugetactic agents include cytokines. In yet other embodiments, the agent suspected of being a fugetactic agent is an agent present in a biological fluid. In preferred embodiments, the biological fluid includes synovial fluid, cerebral spinal fluid, fellopian tube fluid, seminal fluid, ocular fluid, pericardial fluid, pleural fluid, inflammatory exudate and ascitic fluid. In other preferred embodiments, the agent suspected of being a fugetactic agent is an agent present in a tumor cell culture supernatant, tumor cell eluate and/or tumor cell lysate. In some embodiments, the tumor cells are HepG2 cells and the cell with migratory capacity is a hematopoietic cell. In further preferred embodiments, the agent suspected of being a fugetactic agent is an expression product of a cDNA library.

According to another aspect of the invention, a method of repelling immune cells from a material surface is provided. The method involves coating a material surface with an amount of a fugetactic agent effective to repel immune cells from the material surface. In certain embodiments, the material surface is part of an implant. The material comprising the implant may be synthetic material or organic tissue material. Important fugetactic agents, cell-types, and so on, are as described above.

According to another aspect of the invention, a method of screening for an agent that modulates migratory cell-specific fugetactic activity of a fugetactic agent is provided. The method involves forming a mixture comprising a cell with migratory capacity, a fugetactic agent and a candidate anti-fugetactic agent incubating the mixture under conditions which permit binding of the candidate anti-fugetactic agent to the fugetactic agent, determining the level of a test fugetactic activity of the fugetactic agent and the candidate anti-fugetactic agent on the cells with migratory capacity, and comparing the level of the test fugetactic activity to a control level of fugetactic activity determined in the absence of the candidate anti-fugetactic agent. In some embodiments, reduction in the test fugetactic activity level relative to the control level of fugetactic activity, indicates that the candidate anti-fugetactic agent is a lead compound for an anti-fugetactic agent which inhibits the fugetactic activity of the fugetactic agent. In certain other embodiments, an increase in the test fugetactic activity level relative to the control level of fugetactic activity, indicates that the candidate anti-fugetactic agent is a lead compound for an anti-fugetactic agent which increases the fugetactic activity of the fugetactic agent. In certain other embodiments, the fugetactic agent is SDF-1α at a concentration higher than about 1 µg/ml, HIV-1$_{IIIB}$ gp120 at a concentration higher than about 200 ng/ml, non-diluted thymic stromal-cell-derived medium, concentrated thymic cell-derived medium or thymic stromal-cell-derived polypeptide factor, non-diluted HepG2-cell-derived medium, concentrated HepG2-cell-derived medium or HepG2-cell-derived polypeptide factor, inter-α-trypsin inhibitor heavy-chain II precursor (ITI H2), non-diluted Kaposi's Sarcoma Herpes Virus infected cell-derived medium, concentrated Kaposi's Sarcoma Herpes Virus infected cell-derived medium, or Kaposi's Sarcoma Herpes Virus infected cell-derived polypeptide factor.

In other embodiments, the cell with migratory capacity is a hematopoietic cell, a neural cell, an epithelial cell, a mesenchymal cell, an embryonic stem cell, a cell involved in angiogenesis (blood vessel formation), or a germ cell.

According to yet another aspect of the invention, a method of enhancing an immune response in a subject having a condition that involves a specific site, is provided. The method involves locally administering to a specific site in a subject in need of such treatment an anti-fugetactic agent in an amount effective to inhibit immune cell-specific fugetactic activity at the specific site in the subject. In some embodiments, the specific site is a site of a pathogenic infection. In certain embodiments, the specific site is a germ cell-containing site. In further embodiments, the specific site is an area immediately surrounding a tumor. In certain embodiments, the anti-fugetactic agent is a cytokine binding agent. In other embodiments, the cytokine binding agent is an anti-cytokine antibody or a cytokine agonist. In a preferred embodiment the cytokine is SDF-1α.

According to a further aspect of the invention, a method of inhibiting tumor cell metastasis in a subject, is provided. The method involves locally administering to a tumor site in a subject in need of such treatment an anti-fugetactic agent in an amount effective to inhibit metastasis of tumor cells from the tumor site in the subject. In certain embodiments, the anti-fugetactic agent is a cytokine binding agent. In other embodiments, the cytokine binding agent is an anti-cytokine antibody or a cytokine agonist. In a preferred embodiment the cytokine is SDF-1α.

According to another aspect of the invention, a method of inhibiting endothelial cell migration to a tumor site in a subject, is provided. The method involves locally administering to an area surrounding a tumor site in a subject in need of such treatment a fugetactic agent in an amount effective to inhibit endothelial cell migration to the tumor site in the subject. In certain embodiments, the area surrounding the tumor site is not immediate to the tumor site. Important fugetactic agents are as described above.

According to a further aspect of the invention, a method of contraception in a subject, is provided. The method involves administering to a subject in need of such treatment, an anti-fugetactic agent in an amount effective to inhibit germ cell migration in the subject. In certain embodiments, the anti-fugetactic agent is a cytokine binding agent. In some embodiments, the cytokine binding agent is an anti-cytokine antibody or a cytokine agonist. In a preferred embodiment the cytokine is SDF-1α.

According to another aspect of the invention, a method of treating infertility and premature labor, including premature delivery and impending miscarriage, is provided. The method involves administering to a subject in need of such treatment a fugetactic agent in an amount effective to inhibit immune cells from migrating close to a germ cell in the subject. In further embodiments, the administration is local to a germ cell-containing site of the subject.

In any of the foregoing aspects and embodiments of the invention where the fugetactic agent is identified as a polypeptide (e.g., SDF-1α., HIV-1$_{IIIB}$ gp120, ITI H2, etc.), fragments of such polypeptide useful according to the invention are only those with fugetactic activity. A person of ordinary skill in the art could easily determine which fragments have such activity by first creating deletions of the full length polypeptides using methods well known in the art, and testing such fragments for their fugetactic activity according to the teachings of the present invention (see, e.g., Examples).

These and other aspects of the invention, as well as various advantages and utilities, will be more apparent with reference to the detailed description of the preferred embodiments.

BRIEF DESCRIPTION OF THE SEQUENCES

Figure 1A:
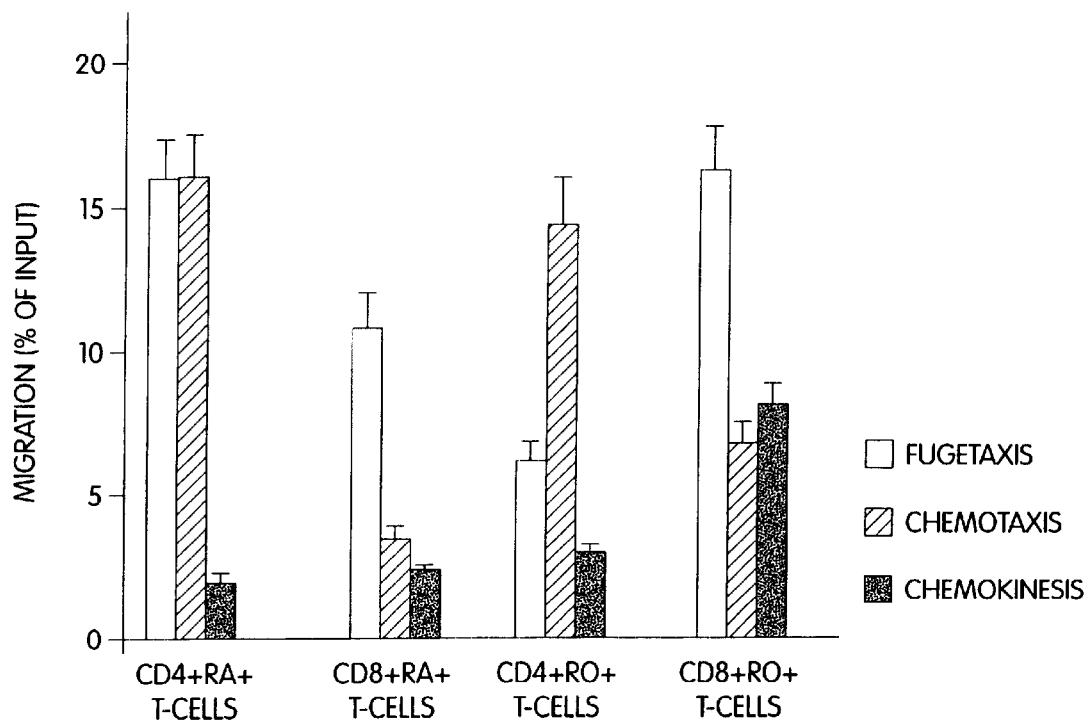
FIG. 1(A). Bar graph showing that SDF-1α induces fugetaxis, chemotaxis and chemokinesis in various T-cell subsets.

SEQ ID NO:1 is the amino acid sequence of inter-α-trypsin inhibitor heavy-chain II precursor (ITI H2) (GenBank Acc. No. P19823).

DETAILED DESCRIPTION OF THE INVENTION

The invention involves the discovery of agents with eukaryotic migratory-cell repellant activity (hereinafter "fugetactic agents" and "fugetactic activity"). The invention also involves the unexpected discovery of agents, previously known to be chemoattractants at defined concentrations, to be acting as fugetactic agents at concentrations higher than the defined concentrations. Pharmaceutical compositions containing the foregoing fugetactic agents, and various therapeutic and diagnostic methods utilizing the foregoing fugetactic agents, are also described in more detail below. The foregoing can be used, inter alia, in the treatment of conditions characterized by a need to modulate migratory-cell movement in specific sites in a subject.

As used herein, a subject is a human, non-human primate, cow, horse, pig, sheep, goat, dog, cat or rodent. In all embodiments, human subjects are preferred.

By "fugetactic activity" it is meant the ability of an agent to repel (or chemorepel) a eukaryotic cell with migratory capacity (i.e., a cell that can move away from a repellant stimulus). Accordingly, an agent with fugetactic activity is a "fugetactic agent." Such activity can be detected using any of the transmigration systems described herein (see Examples), or a variety of other systems well known in the art (see, e.g., U.S. Pat. No. 5,514,555, entitled: "Assays and therapeutic methods based on lymphocyte chemoattractants," issued May 7, 1996, to Springer, T A, et al.).

The present invention relates in part to a novel thymic stromal-cell isolate with fugetactic activity, repelling cells with migratory capacity and in particular mature T cells. Therefore, the thymic stromal-cell isolate is useful generally in conditions where inhibition of migration of immune cells to a specific site is desirable. Such conditions are described in greater detail below and in their majority are associated with an inflammatory response. As described in greater detail below, the thymic stromal-cell isolate is produced by thymic stromal cells. The thymic stromal-cell isolate is protease and heat sensitive, and it elutes-off a typical sepharose ion exchange column with 0.5M NaCl at pH 6.3, and wherein the agent is not SDF-1$\alpha$. In preferred embodiments, the thymic stromal-cell isolate comprises a polypeptide, and it is this polypeptide that repels immune cells. The thymic stromal-cell isolate does not contain an immune cell repelling concentration of SDF-1$\alpha$. An "immune cell repelling concentration of SDF-1$\alpha$," as used herein, is any concentration of SDF-1$\alpha$ higher than about 100 ng/ml. In certain embodiments, an immune cell repelling concentration of SDF-1$\alpha$ is any concentration of SDF-1$\alpha$ higher than about 150 ng/ml. In further embodiments, an immune cell repelling concentration of SDF-1$\alpha$ is any concentration of SDF-1$\alpha$ higher than a concentration selected from the group consisting of about 300 ng/ml, 500 ng/ml, 750 ng/ml, and 1 $\mu$g/ml.

As used herein with respect to thymic stromal-cell isolate, "isolate (i.e. isolated)" means separated from its native environment and present in sufficient quantity to permit its identification or use. Isolated, when referring to a protein or polypeptide, means, for example: (i) selectively produced by expression cloning or (ii) partially purified as by chromatography or electrophoresis. Isolated proteins or polypeptides may, but need not be, substantially pure. In certain embodiments of the present invention the thymic stromal-cell isolate is a substantially pure polypeptide. The term "substantially pure" means that the protein(s) or polypeptide(s) is essentially free of other substances with which it (they) may be found in nature or in vitro systems, to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from many of the substances with which it may be associated in living systems, i.e, isolated from certain other proteins.

The fugetactic polypeptide (or thymic stromal-cell isolate) can be isolated from a non-homogenous proteinaceous solution such as a cell culture supernatant or cell homogenate. Thymic stromal-cells can be isolated from a subject by the disaggregation of a piece of thymic tissue, and forming cell suspensions. These thymic stromal-cell suspensions can be cultured according to standard cell culture techniques. In small scale, the cultures can be contained in culture plates, flasks, and dishes. In larger scale, the cultures can be contained in roller bottles, spinner flasks and other large scale culture vessels such as fermenters. Culturing in a three-dimensional, porous, solid matrix may also be used. In preferred embodiments, thymic stromal-cells are obtained from human fetal thymi of 16 to 22 week abortuses as described in greater detail below.

Conveniently, the thymic stromal-cell isolate can be isolated from the supernatants of the above-described cell cultures, although the entire culture can be homogenized and subjected to the steps described below for isolation of a fugetactic polypeptide (thymic stromal-cell isolate). Typically the supernatant is removed by aspiration or by centrifugation of the cell culture to remove the cells. The cultures can also be filtered to remove cells and cell debris. In important embodiments, the collected supernatant is (in its entirety) the thymic stromal-cell isolate.

The fugetactic polypeptide (thymic stromal-cell isolate)-containing supernatant can be fractionated according to standard chromatographic procedures to facilitate isolation of the fugetactic polypeptide (or thymic stromal-cell isolate). One of ordinary skill in the art will be familiar with such procedures that include, but are not limited to, size-exclusion chromatography, FPLC, HPLC, gel filtration chromatography, ion-exchange chromatography, hydrophobic chromatography, immune-affinity chromatography, etc.

In preferred embodiments, the fractions of thymic stromal-cell isolate containing supernatant then are used to repel immune cells, particularly mature T cells. "Immune cells" as used herein are cells of hematopoietic origin (see later discussion), that are involved in the specific recognition of antigens. Immune cells include antigen presenting cells (APCs), such as dendritic cells or macrophages, B cells, T cells, etc. "Mature T cells" as used herein include T cells of a $CD4^{lo}CD8^{hi}CD69^{+}TCR^{+}$, $CD4^{hi}CD8^{lo}CD69^{+}TCR^{+}$, $CD4^{+}CD3^{+} RO^{+}$ and/or $CD8^{+}CD3^{+}RO^{+}$ phenotype.

The fugetactic response of the mature T cells to the thymic stromal-cell isolate can be measured as described above, or according to the transmigration assays described in greater detail in the Examples. Other suitable methods will be known to one of ordinary skill in the art and can be employed using only routine experimentation.

The fractions which are positive for the thymic stromal-cell isolate can be subjected to additional rounds of screening using the foregoing methodology. The purity of the fraction can be assessed after each round of culture stimulation by subjecting an aliquot of the fraction to SDS-PAGE or other analytical method for visualizing the mixture of constituents in the fraction. The nature of the thymic stromal-cell isolate as a protein, nucleic acid, lipid, carbohydrate etc., can be confirmed at any time by treating an aliquot of a positive fraction with non-specific degradative enzymes for the foregoing classes of molecules and testing the treated fraction in the same assays detailed above.

The thymic stromal-cell isolate can then be further isolated if desired using immunological and molecular biological methods (see, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York). For example, a fraction positive for the thymic stromal-cell isolate (i.e. with fugetactic activity) which is sufficiently purified can be subjected to protein sequencing according to standard methods. For example, the fraction can be subjected to SDS-PAGE, transferred to a membrane such as polyvinylidene fluoride by electroblotting, and N-terminal amino sequence determined by Edman degradation. Any sequence information can be used to screen databases for homology to existing proteins and also to generate degenerate nucleic acids useful for screening a cDNA library by standard methods such as colony hybridization or polymerase chain reaction. Alternatively, the positive fraction can be used to generate antibodies which recognize the thymic stromal-cell isolate. Such antibodies can then be used in expression cloning protocols, Western blots, and other techniques useful in isolation of the thymic stromal-cell isolate. In the foregoing methods, any cDNA libraries, expression libraries, etc., are preferably created from thymic stromal-cells.

The invention also makes it possible to isolate proteins which bind to the thymic stromal-cell isolate as disclosed herein, including antibodies and cellular binding partners of the thymic stromal-cell isolate such as receptors. Once the thymic stromal-cell isolate is isolated according to standard methods known to one of ordinary skill in the art, the thymic stromal-cell isolate (or even a substantially purified cell supernatant or fraction) can be used to generate polyclonal or monoclonal antibodies according to standard methods (see e.g., Harlow and Lane, eds., *Antibodies: A Laboratory Manual*, Cold Spring Harbor Press, Cold Spring Harbor, N.Y., 1988)

The proteins which bind to the thymic stromal-cell isolate can be used, for example, in screening assays to detect the presence or absence of thymic stromal-cell isolate and complexes of thymic stromal-cell isolate and their respective binding partners and in purification protocols to isolate thymic stromal-cell isolate and complexes of thymic stromal-cell isolate and their respective binding partners. The binding proteins also can be used to block the effects of the thymic stromal-cell isolate. Such assays can be used to confirm the specificity of binding.

The invention, therefore, embraces peptide binding agents which, for example, can be antibodies or fragments of antibodies having the ability to selectively bind to thymic stromal-cell isolate and inhibit the fugetactic properties of the isolate or agent (or agent as described above). In important embodiments, the peptide binding agents bind selectively to a substantially pure organic agent that repels mature T-cells. In further important embodiments, the peptide binding agents bind selectively to SDF-1α and inhibits repulsion of immune cells. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons. Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3regions have been replaced by homologous human or non-human sequences; chimeric F(ab')$_2$ fragment antibodies in which the FR and/or CDR1 and/or CDR2 and/or light chain CDR3regions have been replaced by homologous human or non-human sequences; chimeric Fab fragment antibodies in which the FR and/or CDR1 and/or CDR2 and/or light chain CDR3regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to thymic stromal-cell isolate, and complexes of both thymic stromal-cell isolate and its binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

As detailed herein, the foregoing antibodies and other binding molecules may be used for example to identify tissues expressing protein or to purify protein. Antibodies also may be coupled to specific diagnostic labeling agents for imaging of cells and tissues that express a thymic stromal-cell isolate.

The invention in another part relates to the unexpected discovery that agents previously known to be acting as chemoattractants of immune cells at defined concentrations, also act as fugetactic agents to the same cells at concentrations higher than the defined concentrations. In a preferred embodiment, such fugetactic agents include cytokines. "Cytokine" is a generic term for nonantibody soluble proteins which are released from one cell subpopulation and which act as intercellular mediators, for example, in the generation or regulation of an immune response. See Human Cytokines: Handbook for Basic & Clinical Research (Aggrawal, et al. eds., Blackwell Scientific, Boston, Mass. 1991) (which is hereby incorporated by reference in its entirety for all purposes). Cytokines include, e.g., interleukins IL-1 through IL-15, tumor necrosis factors α & β, interferons α, β, and γ, tumor growth factor beta (TGF-β), colony stimulating factor (CSF) and granulocyte monocyte colony stimulating factor (GM-CSF). The action of each cytokine on its target cell is mediated through binding to a cell surface receptor. Cytokines share many properties of hormones, but are distinct from classical hormones in that in vino, they generally act locally on neighboring cells within a tissue. The activities of cytokines range from promoting cell growth (e.g., IL-2, IL-4, and IL-7), and arresting growth (IL-10, tumor necrosis factor and TGF-β ), to inducing viral resistance (IFN α, β, and γ). See Fundamental Immunology (Paul ed., Raven Press, 2nd ed. 1989): Encyclopedia of Immunology. (Roitt ed., Academic Press 1992) (which are hereby incorporated by reference in their entirety for all purposes). In certain embodiments, the cytokine is a cytokine with chemoattractant and/or chemokinetic properties. Examples of such cytokines include: PAF, N-formylated peptides, C5a, LTB$_4$, LXA$_4$, chemokines: CXC, IL-8, GCP-2, GROα, GROβ, GROγ, ENA-78, NAP-2, IP-10, MIG, I-TAC, SDF-1α, BCA-1, PF4, Bolekine, MIP-1α, MIP-1β, RANTES, HCC-1, MCP-1, MCP-2, MCP-3, MCP-4, MCP-5 (mouse only), Leukotactin-1 (HCC-2, MIP-5), Eotaxin, Eotaxin-2 (MPIF2), Eotaxin-3 (TSC), MDC, TARC, SLC (Exodus-2, 6CKine), MIP-3α (LARC, Exodus-1), ELC (MIP-3β), I-309, DC-CK1 (PARC, AMAC-1), TECK, CTAK, MPIF1 (MIP-3), MIP-5 (HCC-2), HCC-4 (NCC-4), MIP-1γ (mouse only), C- 10 (mouse only); C: Lymphotactin; CX$_3$C: Fracktelkine (Neurotactin). Most preferably, the cytokine is a member of the Cys-X-Cys family of chemokines (chemokines that bind to the CXCR-4 receptor). Preferred such agents of the invention include SDF-1α, SDF-1β, and met-SDF-1β. In further preferred embodiments, such fugetactic agents include other CXCR-4 receptor ligands. CXCR-4 ligands include, but are not limited to, HIV-1$_{IIIB}$ gp120, small molecules T134 and MD3100, and/or T22 ([Tyr5,12,Lys7]-polyphemusin II) (Heveker et al., Curr Biol, 1998, 8:369–76).

SDF-1α is a cytokine (chemokine) produced by thymic and bone marrow stroma ([12-15] and U.S. Pat. No. 5.756,084, entitled: "Human stromal derived factor 1α and 1β," issued May 26, 1998, to Honjo, et al.), that has been reported as a highly efficacious and highly potent lymphocyte chemoattractant at concentrations lower than about 100 ng/ml. We have discovered, unexpectedly, that SDF-1α at a concentration higher than about 200 ng/ml, and preferably higher than about 1 µg/ml, acts a potent fugetactic agent to immune cells, and more specifically to mature T cells, as described in greater detail in the Examples.

Recombinant envelope glycoprotein gp120 of substrain IIIB of HIVLAI (HIV-1$_{IIIB}$ gp120) has been used extensively in the art to generate neutralizing antibodies to HIV. The association between gp120 and the CXCR-4 co-receptor for efficient HIV entry into a cell has also been established (Stott E J, et al., J Gen Virol, 1998, 79(Pt3):423–32). We have discovered, that HIV-1$_{IIIB}$ gp120 at a concentration higher than about 10 ng/ml, and preferably higher than about 200 ng/ml, acts a potent fugetactic agent to immune cells, and more specifically to mature T cells, as described in greater detail in the Examples.

The invention in another aspect involves a method for isolating a stromal-cell derived fugetactic agent. According to the method, a culture of stromal-cells is first prepared. Stromal cells comprising fibroblasts with or without other cells and elements described below (the term "fibroblasts" is used collectively herein to include such cells), are inoculated onto a tissue culture vessel (a typical two-dimensional culture dish or three-dimensional matrix). These fibroblasts may be derived from tissues or organs that include, but are not limited to, skin, liver, pancreas, bone marrow, lymph node, thymus, kidney, CNS, brain, etc., which can be obtained by biopsy (where appropriate) or upon autopsy. In fact fibroblasts can be obtained in quantity rather conveniently from any appropriate cadaver organ. Fetal fibroblasts can also be used.

Fibroblasts may be readily isolated by disaggregating an appropriate organ or tissue which is to serve as the source of the fibroblasts. This may be readily accomplished using techniques known to those skilled in the art. For example, the tissue or organ can be disaggregated mechanically and/or treated with digestive enzymes and/or chelating agents that weaken the connections between neighboring cells, making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase. DNase, pronase, dispase, etc. Mechanical disruption can also be accomplished by a number of methods including, but not limited to, the use of grinders blenders, sieves, homogenizers, pressure cells, or insonators to name but a few. For a review of tissue disaggregation techniques, see Freshney, Culture of Animal Cells, A Manual of Basic Techniques, 2d Ed., A. R. Liss, Inc., New York, 1987, Ch. 9, pp. 107–126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, *Culture of Animal Cells,* A Manual of Basic Techniques, 2d Ed., A. R. Liss, Inc., New York, 1987, Ch. 11 and 12, pp. 137–168.

The isolation of fibroblasts may, for example, be carried out as follows: fresh tissue samples are thoroughly washed and minced in Hank's balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional matrix (see, Naughton et al., 1987, *J. Med.,* 18:219–250). Inoculation of the culture vessel with a high concentration of stromal cells, e.g., approximately $10^6$ to $5 \times 107$ cells/ml, will result in the establishment of a confluent stromal-cell culture in shorter periods of time.

As mentioned above, other stromal-cells found in loose connective tissue may be inoculated onto the culture vessel along with the fibroblasts. These stromal-cells may readily be derived from the same appropriate organs the fibroblasts are derived, that include, but are not limited to, skin, liver, pancreas, bone marrow, lymph node, thymus, kidney, CNS, brain, etc., using methods known in the art such as those discussed above. Such cells include, but are not limited to, endothelial cells, pericytes, macrophages, monocytes, plasma cells, mast cells, adipocytes, etc. In one example, stromal cells of hematopoietic tissue, including but not limited to, fibroblasts, endothelial cells, macrophages/monocytes, adipocytes and reticular cells, could be used to inoculate a tissue culture dish and/or a three-dimensional matrix.

Hematopoietic stromal-cells may be readily obtained from the "buffy coat" formed in bone marrow suspensions by centrifugation at low forces, e.g., 3000 g. Stromal-cells of liver may include fibroblasts, Kupffer cells, and vascular and bile duct endothelial cells. Similarly, glial cells could be used as the stroma to support the proliferation of neurological cells and tissues; glial cells for this purpose can be obtained by trypsinization or collagenase digestion of embryonic or adult brain (Ponten and Westermark, 1980, in Federolf S. Hertz. L., eds, *Advances in Cellular Neurobiology,* Vol. 1, New York, Academic Press, pp.209–227).

After inoculation of the stromal cells, the vessel is incubated in an appropriate nutrient medium under conditions that are metabolically favorable for the growth of the cells. As used herein, the phrase "metabolically favorable conditions" refers to conditions that promote cell division. Such conditions include growth in nutrient medium at 37° C. in a 5% $CO_2$ incubator with greater than 90% humidity. Many commercially available media, such as RPMI 1640. Fisher's, Iscove's, McCoy's, Dulbecco's Modified Eagle's Medium, etc., and the like, which may or may not be supplemented with serum, may be suitable for use as nutrient medium. Antibiotics such as penicillin and streptomycin may also be included. In preferred embodiments, the stromal cells are cultured first, for a brief period of time (e.g., at least 1 hour), in the presence of 10% serum. The medium is then changed to a serum-free medium in order to minimize the number of extraeneous (i.e. nonstromal-cell derived) agents that would be present in the medium under continuous culture. The serum-free stromal-cell medium is therefore going to become a stromal-cell conditioned medium (supernatant) upon the continuous incubation of the stromal-cells.

Newly inoculated cultures may be allowed to grow under metabolically favorable conditions for between about 3–6 cell cycles. A cell cycle, as defined herein, is the length of time between mitoses. Preferably, the stromal-cells are grown to confluency (for example, at a concentration of of $10^7$ cells/10 ml medium in suspension).

The supernatant from the culture of stromal-cells is then isolated. Typically, the supernatant is removed by aspiration or by centrifugation of the cell culture to remove the cells. The cultures can also be filtered to remove cells and cell-debris. The supernatant (which is suspected of containing a fugetactic agent) is then fractionated into a plurality of fractions, and a fraction from the plurality of fractions is contacted with a cell with migratory capacity. A "cell with migratory capacity" is a eukaryotic cell that includes, but is not limited to, a cell of hematopoietic origin, a cell of neural origin, a cell of epithelial origin, a cell involved in angiogenesis, a cell of mesenchymal origin, an embryonic stem cell, or a germ cell, Such cells with migratory capacity can respond to a variety of chemotactic signals, including chemoattractive and chemorepulsive (fugetactic) signals. The response typically involves changes in the actin cytoskeleton.

Cells of "hematopoietic origin" include, but are not limited to, pluripotent stem cells, multipotent progenitor cells and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage. The hematopoietic cells may be derived from a tissue such as bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue includes the thymus, spleen, liver, lymph node, skin, tonsil and Peyer's patches. In other embodiments, the "hematopoietic origin" cells may be derived from in vitro cultures of any of the foregoing cells, and in particular in vitro cultures of progenitor cells.

Cells of neural origin, include neurons and glia, and/or cells of both central and peripheral nervous tissue that express RR/B (sec, U.S. Pat. No. 5,863,744, entitled: "Neural cell protein marker RR/B and DNA encoding same," issued Jan. 26, 1999, to Avraham, et al.).

Cells of epithelial origin, include cells of a tissue that covers and lines the free surfaces of the body. Such epithelial tissue includes cells of the skin and sensory organs, as well as the specialized cells lining the blood vessels, gastrointestinal tract, air passages, ducts of the kidneys and endocrine organs.

Cells of mesenchymal origin include cells that express typical fibroblast markers such as collagen, vimentin and fibronectin.

Cells involved in angiogenesis are cells that are involved in blood vessel formation and include cells of epithelial origin and cells of mesenchymal origin.

An embryonic stem cell is a cell that can give rise to cells of all lineages; it also has the capacity to self-renew.

A germ cell is a cell specialised to produce haploid gametes. It is a cell further differentiated than a stem cell, that can still give rise to more differentiated germ-line cells.

Movement of the cell with migratory capacity is then measured according to any of the methods decribed elsewhere herein (e.g., see Examples), and a person of ordinary skill in the art may determine whether the movement of the cell with migratory capacity is movement away from the fraction. Such movement of the cell with migratory capacity away from the fraction is indicative of the presence of a fugetactic agent in the fraction.

The fugetactic agent (stromal or other -cell isolate)-containing supernatant can be fractionated according to standard chromatographic procedures to facilitate isolation of the fugetactic polypeptide (thymic stromal or other -cell isolate). One of ordinary skill in the art will be familiar with such procedures that include, but are not limited to, size-exclusion chromatography, FPLC, HPLC, gel filtration chromatography, ion-exchange chromatography, hydrophobic chromatography, immune-affinity chromatography, etc. (see also the Examples section).

In certain embodiments, the stromal-cells are thymic stromal-cells and the cell with migratory capacity is a hematopoietic cell. In other embodiments, the stromal-cells are isolated from an immune-privileged site/tissue. An "immune-privileged tissue" is a tissue with immune-cell tolerance and includes, but is not limited to, brain tissue, central nervous system (CNS), testes, placenta, or ocular tissue (e.g., aqueous humour).

Other fugetactic molecules can be isolated from different tissues or biological fluid homogenates or supernatants, or other biological materials, using the foregoing methodology. In preferred embodiments, the biological fluid includes, but is not limited to, synovial fluid, cerebral spinal fluid, fallopian tube fluid, seminal fluid, ocular fluid, pericardial fluid, pleural fluid, inflammatory exudate and ascitic fluid.

In other preferred embodiments, the agent suspected of being a fugetactic agent is an agent present in a tumor cell culture supernatant, tumor cell eluate, and/or tumor cell lysate (see also the Examples section). The tumor cell may be of a cancer or tumor type thought to escape immune recognition. Such cancers or tumors may be of the folowing origin: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, colon carcinoma, colorectal cancer, lymphoid cell-derived leukemia, choriocarcinoma, and melanoma.

In any of the foregoing embodiments, the cell with migratory capacity is a hematopoietic cell. In preferred embodiments, the hematopoietic cell is an immune cell.

According to another aspect, the invention involves a method of repelling immune cells from a material surface. "Material surfaces" as used herein, include, but are not limited to, dental and orthopedic prosthetic implants, artificial valves, and organic implantable tissue such as a stent, allogeneic and/or xenogeneic tissue, organ and/or vasculature.

Implantable prosthetic devices have been used in the surgical repair or replacement of internal tissue for many years. Orthopedic implants include a wide variety of devices, each suited to fulfill particular medical needs. Examples of such devices are hip joint replacement devices, knee joint replacement devices, shoulder joint replacement devices, and pins, braces and plates used to set fractured bones. Some contemporary orthopedic and dental implants, use high performance metals such as cobalt-chrome and titanium alloy to achieve high strength. These materials are readily fabricated into the complex shapes typical of these devices using mature metal working techniques including casting and machining.

The material surface is coated with an amount of a fugetactic agent effective to repel immune cells. In important embodiments, the material surface is part of an implant. In important embodiments, in addition to a fugetactic agent, the material surface may also be coated with a cell-growth potentiating agent, an anti-infective agent, and/or an antiinflammatory agent.

A cell-growth potentiating agent as used herein is an agent which stimulates growth of a cell and includes growth factors such as PDGF, EGF, FGF, TGF, NGF, CNTF, and GDNF.

An anti-infectious agent as used herein is an agent which reduces the activity of or kills a microorganism and includes: Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride, Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin lydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacil; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz: Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter: Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloridc; Tetracycline Phosphate Complex; Tetroxoprim; Thiamphenicol; Thiphencillin Potassium; Ticarcillin Cresyl Sodium: Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride.

Antiinflammatory agents are as described below.

According to one aspect of the invention, a method of inhibiting migration of immune cells to a specific site in a subject is provided. The method involves locally administering to a specific site in a subject in need of such treatment a fugetactic agent in an amount effective to inhibit migration of immune cells to the specific site in a subject.

In one important embodiment, the invention provides a method of inhibiting migration of immune cells to a site of inflammation in the subject, "Inflammation" as used herein, is a localised protective response elicited by a foreign (non-self) antigen, and/or by an injury or destruction of tissue(s), which serves to destroy, dilute or sequester the foreign antigen, the injurious agent, and/or the injured tissue. Inflammation occurs when tissues are injured by viruses, bacteria, trauma, chemicals, heat, cold, or any other harmful stimuli. In such instances, the classic weapons of the immune system (T cells, B cells, macrophages) interface with cells and soluble products that are mediators of inflammatory responses (neutrophils, eosinophils, basophils, kinin and coagulation systems, and complement cascade).

A typical inflammatory response is characterized by (i) migration of leukocytes at the site of antigen (injury) localization; (ii) specific and nonspecific recognition of "foreign" and other (necrotic/injured tissue) antigens mediated by B and T lymphocytes, macrophages and the alternative complement pathway; (iii) amplification of the inflammatory response with the recruitment of specific and nonspecific effector cells by complement components, lymphokines and monokines, kinins, arachidonic acid metabolites, and mast cell/basophil products; and (iv) macrophage, neutrophil and lymphocyte participation in antigen destruction with ultimate removal of antigen particles (injured tissue) by phagocytosis. The ability of the immune system to discriminate between "self" and "non-self" (foreign) antigens is therefore vital to the functioning of the immune system as a specific defense against "non-self" antigens.

"Non-self" antigens are those antigens on substances entering a subject, or exist in a subject but are detectably different or foreign from the subject's own constituents, whereas "self" antigens are those which, in the healthy subject, are not detectably different or foreign from its own constituents. However, under certain conditions, including in certain disease states, an individual's immune system will identify its own constituents as "non-self," and initiate an immune response against "self-antigens," at times causing more damage or discomfort as from, for example, an invading microbe or foreign material, and often producing serious illness in a subject.

In another important embodiment, the inflammation is caused by an immune response against "self-antigen," and the subject in need of treatment according to the invention has an autoimmune disease. "Autoimmune disease" as used herein, results when a subject's immune system attacks its own organs or tissues, producing a clinical condition associated with the destruction of that tissue, as exemplified by diseases such as rheumatoid arthritis, uveitis. insulin-dependent diabetes mellitus, hemolytic anemias, rheumatic fever, Crohn's disease. Guillain-Barre syndrome, psoriasis, thyroiditis, Graves' disease, myasthenia gravis. glomerulonephritis, autoimmune hepatitis, multiple sclerosis, systemic lupus erythematosus, etc.

Autoimmune disease may be caused by a genetic predisposition alone, by certain exogenous agents (e.g., viruses, bacteria, chemical agents, etc.), or both. Some forms of autoimmunity arise as the result of trauma to an area usually not exposed to lymphocytes, such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of a subject to antigens which are antigenically similar to, that is cross-reactive with, the subject's own tissue. In rheumatic fever, for example, an antigen of the streptococcal bacterium, which causes rheumatic fever, is cross-reactive with parts of the human heart. The antibodies cannot differentiate between the bacterial antigens and the heart muscle antigens, consequently cells with either of those antigens can be destroyed.

Other autoimmune diseases, for example, insulin-dependent diabetes mellitus (involving the destruction of the insulin producing beta-cells of the islets of Langerhans), multiple sclerosis (involving the destruction of the conducting fibers of the nervous system) and rheumatoid arthritis (involving the destruction of the joint-lining tissue), are characterized as being the result of a mostly cell-mediated autoimmune response and appear to be due primarily to the action of T cells (See, Sinha et al., *Science*, 1990, 248:1380). Yet others, such as myesthenia gravis and systemic lupus erythematosus, are characterized as being the result of primarily a humoral autoimmune response. Nevertheless, inhibition of migration of immune cells to a specific site of inflammation involved in any of the foregoing conditions according to the invention, is beneficial to the subject since it inhibits escalation of the inflammatory response, protecting the specific site (e.g., tissue) involved, from "self-damage." In preffered embodiments, the subject has rheumatoid arthritis, multiple sclerosis, or uveitis.

In a further important embodiments, the inflammation is caused by an immune response against "non-self-antigens" (including antigens of necrotic self-material), and the subject in need of treatment according to the invention is a transplant recipient, has atherosclerosis, has suffered a myocardial infarction and/or an ischemic stroke, has an abscess, and/or has myocarditis. This is because after cell (or organ) transplantation, or after myocardial infarction or ischemic stroke, certain antigens from the transplanted cells (organs), or necrotic cells from the heart or the brain, can stimulate the production of immune lymphocytes and/or autoantibodies, which later participate in inflammation/rejection (in the case of a transplant), or attack cardiac or brain target cells causing inflammation and aggravating the condition (Johnson et al., *Sem. Nuc. Med.* 1989, 19:238:Leinonen et al., *Microbiol. Path.*, 1990, 9:67; Montalban et al., *Stroke*, 1991, 22:750).

According to yet another aspect of the invention, a method of enhancing an immune response in a subject having a condition that involves a specific site, is provided. The method involves locally administering to a specific site in a subject in need of such treatment an anti-fugetactic agent in an amount effective to inhibit immune cell-specific fugetactic activity at a specific site in the subject. In some embodiments, the specific site is a site of a pathogenic infection. Efficient recruitment of immune cells to help eliminate the infection is therefore beneficial.

In certain embodiments, the specific site is a germ cell containing site. In this case the recruitment of immune cells to these specific sites will help eliminate unwanted germ cells, and/or implanted and nonimplanted embryos. In further embodiments, co-administration of contraceptive agents other than anti-fugetactic agents is also provided. Non-anti-fugetactic contraceptive agents are well known in the art.

In further embodiments, the specific site is an area immediately surrounding a tumor. Since most of the known tumors escape immune recognition, it is beneficial to enhance the migration of immune cells to the tumor site. In further embodiments, co-administration of anti-cancer agents other than anti-fugetactic agents is also provided. Non-anti-fugetactic anti-cancer agents include: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexatc; Eflorithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatini; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Podofilox; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxotere; Tecogalan Sodium; Tegafur, Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporlin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate Virlrosidine Sulfate; Vinzolidine Sulfate; Vorozole; Zeniplatin; Zinostatin; Zorubicin Hydrochloride.

According to a further aspect of the invention, a method of inhibiting tumor cell metastasis in a subject, is provided. The method involves locally administering to a tumor site in a subject in need of such treatment an anti-fugetactic agent in an amount effective to inhibit metastasis of tumor cells from the tumor site in the subject. In certain embodiments, the anti-fugetactic agent is a cytokine binding agent. In other embodiments, the cytokine binding agent is an anti-cytokine antibody or a cytokine agonist. In a preferred embodiment the cytokine is SDF-1α. In further embodiments, co-administration of anti-cancer agents other than anti-fugetactic agents is also provided. Anti-cancer agents are as described above.

According to another aspect of the invention, a method of inhibiting endothelial cell migration to a tumor site in a subject, is provided. The method involves locally administering to an area surrounding a tumor site in a subject in need of such treatment a fugetactic agent in an amount effective to inhibit endothelial cell migration to the tumor site in the subject. In certain embodiments, the area surrounding the tumor site is not immediate to the tumor site. Important fugetactic agents are as described above.

According to a further aspect of the invention, a method of contraception in a subject, is provided. The method involves administering to a subject in need of such treatment, an anti-fugetactic agent in an amount effective to inhibit migration of germ cells in the subject. In certain embodiments, the anti-fugetactic agent is a cytokine binding agent. In some embodiments, the cytokine binding agent is an anti-cytokine antibody or a cytokine agonist. In a preferred embodiment the cytokine is SDF-1α. In further embodiments, the administration is local to a germ cell-containing site of the subject.

According to another aspect of the invention, a method of treating infertility and premature labor, including premature delivery and impending miscarriage, is provided. The method involves administering to a subject in need of such treatment a fugetactic agent in an amount effective to inhibit immune cells from migrating close to a germ cell (including an egg, a sperm, a fertilized egg, or an implanted embryo) in the subject. In further embodiments, the administration is local to a germ cell-containing site of the subject. The foregoing methods of therapy may include co-administration of a non-fugetactic agent together with a fugetactic agent of the invention that can act cooperatively, additively, or synergistically with the fugetactic agent of the invention to inhibit migration of immune cells to the site of inflammation in the subject. According to some embodiments, a fugetactic agent is administered substantially simultaneously with a non-fugetactic agent to inhibit migration of immune cells to a site of inflammation. By "substantially simultaneously," it is meant that the fugetactic agent is locally administered to the subject close enough in time with the administration of the non-fugetactic agent, whereby the non-fugetactic agent may exert a potentiating effect on migration inhibiting activity of the fugetactic agent. Thus, by substantially simultaneously it is meant that the fugetactic agent is administered before, at the same time, and/or after the administration of the non-fugetactic agent. The fugetactic agent can be administered as a polypeptide, and/or a nucleic acid which expresses a fugetactic agent.

In certain embodiments, the non-fugetactic agents are immunosuppressants. Such immunosuppressants include: Azathioprine; Azathioprine Sodium: Cyclosporine; Daltroban; Gusperimus Trihydrochloride; Sirolimus; Tacrolimus.

In other embodiments, the non-fugetactic agents are anti-inflammatory agents. Such anti-inflammatory agents include: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

The compositions, as described above, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is a local (site-specific) reduction of inflammation. In other cases, it is inhibition of tumor growth and/or metastasis.

Generally, doses of active compounds of the present invention would be from about 0.01 mg/kg per day to 1000 mg/kg per day. It is expected that doses ranging from 50–500 mg/kg will be suitable. A variety of administration routes are available. The methods of the invention, generally speaking may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694–1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The fugetactic agents, fugetactic binding agents, or fragments thereof may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The invention in other aspects includes pharmaceutical compositions of fugetactic agents and anti-fugetactic agents.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Fugetactic molecules (nucleic acids or polypeptides) preferably are produced recombinantly, although such molecules may be isolated from biological extracts. Recombinantly produced fugetactic agents such as SDF-1α polypeptides, include chimeric proteins comprising a fusion of a SDF-1α protein with another polypeptide, e.g., a polypeptide capable of providing or enhancing protein-protein binding, sequence specific nucleic acid binding (such as GAL4), enhancing stability of the SDF-1α polypeptide under assay conditions, or providing a detectable moiety, such as green fluorescent protein. A polypeptide fused to a SDF-1α polypeptide or fragment may also provide means of readily detecting the fusion protein, e.g., by immunological recognition or by fluorescent labeling.

Various techniques may be employed for introducing nucleic acids of the invention (SDF-1α sense and anti-sense, dominant negative) into cells, depending on whether the nucleic acids are introduced in vitro or in vivo in a host. Such techniques include transfection of nucleic acid-CaPO$_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the fugetactic agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667, 014, 4,748,034 and 5,239,660 and (b) difusional systems in which an active component permeates at a controlled rate from a polymer such as described in U.S. Pat. Nos. 3,832, 253, and 3,854,480.

A preferred delivery system of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV). which range in size from 0.2–4.0 µm can encapsulate large macromolecules. RNA, DNA, and intact virions can be encapsulated within the aqueous interior and be delivered to cells in a biologically active form (Fraley, et al., *Trends Biochem. Sci.,* (1981) 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells: (3) delivery of the aqueous contents of the vesicle to the target cell cytoplasm at high efficiency: and (4) accurate and effective expression of genetic information.

Liposomes may be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N, N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology,* (1985) 3:235–241.

In one important embodiment, the preferred vehicle is a biocompatible microparticle or implant that is suitable for implantation into the mammalian recipient. Exemplary bioerodible implants that are useful in accordance with this method are described in PCT International application No. PCT/US/03307 (Publication No. WO 95/24929, entitled "Polymeric Gene Delivery System"). PCT/US/0307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the fugetactic agents described herein are encapsulated or dispersed within the biocompatible, preferably biodegradable polymeric matrix disclosed in PCT/US/03307.

The polymeric matrix preferably is in the form of a microparticle such as a microsphere (wherein a fugetactic agent is dispersed throughout a solid polymeric matrix) or a microcapsule (wherein a fugetactic agent is stored in the core of a polymeric shell). Other forms of the polymeric matrix for containing a fugetactic agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used. Preferably when an aerosol route is used the polymeric matrix and fugetactic agent are encompassed in a surfactant vehicle. The polymeric matrix composition can be selected to have both favorable degradation rates and also to be formed of a material which is bioadhesive, to further increase the effectiveness of transfer. The matrix composition also can be selected not to degrade, but rather, to release by diffusion over an extended period of time.

In another important embodiment the delivery system is a biocompatible microsphere that is suitable for local, site-specific delivery. Such microspheres are disclosed in Chickering et al., *Biotech. And Bioeng.,* (1996) 52:96–101 and Mathiowitz et al., *Nature,* (1997) 386:410–414.

Both non-biodegradable and biodegradable polymeric matrices can be used to deliver the fugetactic agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, fugetactic agents are delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly (hexylmethacrylate), poly(isodecyl methacrylate), poly (lauryl methacrylate), poly(phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in *Macromolecules.* (1993) 26:581–587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly (isobutyl methacrylate), poly(hexylmethacrylate), poly (isodecyl methacrylate), poly(lauryl methacrylate), poly (phenyl methacrylate), poly(methyl acrylate), poly (isopropyl acrylate), poly(isobutyl acrylate), and poly (octadecyl acrylate).

In addition, important embodiments of the invention include pump-based hardware delivery systems, some of which are adapted for implantation. Such implantable pumps include controlled-release microchips. A preferred controlled-release microchip is described in Santini, J T Jr. et al., *Nature,* 1999, 397:335–338, the contents of which are expressly incorporated herein by reference.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In certain embodiments, the isolated fugetactic agents of the invention are delivered directly to the site at which there is inflammation, e.g., the joints in the case of a subject with rheumatoid arthritis, the blood vessels of an atherosclerotic organ, etc. For example, this can be accomplished by attaching an isolated fugetactic molecule (nucleic acid or polypeptide) to the surface of a balloon catheter; inserting the catheter into the subject until the balloon portion is located at the site of inflammation, e.g. an atherosclerotic vessel, and inflating the balloon to contact the balloon surface with the vessel wall at the site of the occlusion. In this manner, the compositions can be targeted locally to particular inflammatory sites to modulate immune cell migration to these sites. In another example the local administration involves an implantable pump to the site in need of such treatment. Preferred pumps are as described above. In a further example, when the treatment of an abscess is involved, the fugetactic agent may be delivered topically, e.g., in an ointment/dermal formulation. Optionally, the fugetactic molecules of the invention are delivered in combination with a non-fugetactic molecule (e.g., antiinflammatory, immunosuppressant, etc).

In a preferred embodiment of the invention, the isolated fugetactic agents of the invention are administered to a subject in combination with a balloon angioplasty procedure. A balloon angioplasty procedure involves inserting a catheter having a deflated balloon into an artery. The deflated balloon is positioned in proximity to the atherosclerotic plaque and the site of inflammation, and is inflated such that the plaque is compressed against the arterial wall. As a result, the layer of endothelial cells on the surface of the artery is disrupted. thereby exposing the underlying vascular smooth muscle cells. The isolated fugetactic molecule is attached to the balloon angioplasty catheter in a manner which permits release of the isolated fugetactic molecule at the site of the atherosclerotic plaque and the site of inflammation. The isolated fugetactic molecule may be attached to the balloon angioplasty catheter in accordance with standard procedures known in the art. For example, the isolated fugetactic molecule may be stored in a compartment of the balloon angioplasty catheter until the balloon is inflated, at which point it is released into the local environment. Alteratively, the isolated fugetactic molecule may be impregnated on the balloon surface, such that it contacts the cells of the arterial wall as the balloon is inflated. The fugetactic molecule also may be delivered in a perforated balloon catheter such as those disclosed in Flugelman, et al., *Circulation,* v. 85, p. 1110–1117 (1992). See, also, e.g., published PCT Patent Application WO 95/23161, for an exemplary procedure for attaching a therapeutic protein to a balloon angioplasty catheter. This procedure can be modified using no more that routine experimentation to attach a therapeutic nucleic acid to the balloon angioplasty catheter.

The invention will be more fully understood by reference to the following examples. These examples, however, are merely intended to illustrate the embodiments of the invention and are not to be construed to limit the scope of the invention.

EXAMPLES

Materials and Methods

Adult Human Venous Blood Sampling and Sorting of Subpopulations of Peripheral Blood T-cells Peripheral blood was obtained from 12 healthy donors (age 25–40 years, median age 31). Peripheral blood mononuclear cells (PBMC) were obtained from peripheral blood using Ficoll-Hypaque. PBMC were stained with anti-CD4 (PE), anti-CD8 (PE), anti-CD45RA (FITC), anti-CD45RO (FITC) (Becton-Dickinson, San Jose, Calif.). The CD4$^+$45RA$^+$, CD4$^+$CD45RO$^+$ and CD8$^+$CD45RA$^+$ or CD8$^+$CD45RO$^+$ subpopulations of peripheral blood cells were sorted using a FACS vantage sorter (Becton-Dickinson, San Jose, Calif.). The purity of each T-cell subpopulation was determined to be greater than 99%) by immunophenotyping.

Chemokine receptor expression including mean fluorescent intensities for chemokine receptors were also measured and compared for each T-cell subpopulation by staining sorted cells with anti-CXCR4 (PE) (Pharmagen/Becton Dickinson, San Diego, Calif.) directed against the cellular receptor for SDF-1α. Sorted adult peripheral blood T-cell subpopulations were cultured overnight in serum-free Iscoves modified medium ((GIBCO BRL, Gaithersburg, Md.), prior to their use in chemotaxis assays.

Processing of Human Fetal Thymi and Fetal Blood and the Preparation of Purified Subpopulations of Human Fetal Thymocytes and Fetal Blood T-cells Human fetal thymi and peripheral blood samples were obtained from 16 to 22 week abortuses according to Institutional Review Board approved guidelines. Thymi were physically disaggregated and mononuclear cell suspensions generated. Thymocytes were stained with CD8 (FITC), CD3 (PE) and CD4 (APC) and sorted into purified subpopulations of triple negative immature thymocytes (TN) (CD3$^-$, CD4$^-$, CD8$^-$) and mature double positive (DP) (CD4$^+$CD8$^+$) and single positive (SP) thymocytes (CD3$^+$CD4$^+$ or CD3$^+$CD8$^+$) by cell sorting. Fetal blood mononuclear cells (FBMC) were prepared from fetal blood using Ficoll-Hypaque as above. FBMC were labeled with CD8 (FITC), CD3 (PE), CD4 (APC) and anti-CD45RA (FITC). Purified populations of CD4$^+$CD45RA$^+$ and CD8$^+$CD45RA$^+$ T-cells were sorted cultured overnight in serum free Iscoves modified medium prior to use in chemotaxis assays.

Transmigration Assays: Use of SDF-1α

Three chemotaxis assays were used in this study. First, quantitative chemotaxis transmigration assays were performed using a transwell system (Corning Inc., NY) (6.5 mm diameter, 5 μm pore size, polycarbonate membrane) as previously described [13]. Purified T-cell and thymocyte subpopulations ($5 \times 10^4$ cells) were added to the upper chamber of each well in a total volume of 150 μl of IMDM alone. SDF-1α (PeproTech, Rocky Hill, N.J.) was used at concentrations of 10 μg/ml, 1 μg/ml, 100 ng/ml, 10 ng/ml and 0 ng/ml in the lower, upper or both lower and upper chambers of the transwell to generate a checkerboard analysis matrix of positive, negative and absent gradients of SDF-1α respectively. Cells were pretreated with pertussis toxin (PTX) 100 ng/ml for 1 hour, genistein (1 μg/ml for 20 minutes), herbimycin (1 μM for 20 minutes) or wortmannin (1 μM for 20 minutes) (Sigma Chemical Company, St Louis, Mo.) in a tissue culture incubator at 37° C. and 5% $CO_2$ prior to their addition to the upper chambers of the transwells in selected experiments.

Transwells prepared in this way were incubated for 3 hours at 37° C., 5% $CO_2$ incubator. Cells were harvested from the lower chamber after 3 hours and cell counts, immunophenotype and CXCR-4 chemokine receptor expression determined.

The second semi-quantitative transmigration assay involved the use of a tissue culture insert (6.5 mm diameter, 0.45 μm pore size, polycarbonate membrane) (Millipore, Bedford Mass.). Adult peripheral blood T-cell subpopulations ($1 \times 10^5$ cells) were plated into the wells of a 12-well tissue-culture dish in serum-free Iscove's medium. The tissue-culture plate was then incubated at 37° C. for 1 hour to allow the cells to settle evenly over the base of the well. 0.1 ml of IMDM containing SDF-1α at final concentrations of 10 μg/ml, 1 μg/ml, 100 ng/ml, 10 ng/ml or 0 ng/ml was then dispensed into the tissue culture insert. The tissue culture insert was gently placed in the center of the well of the 12-well tissue-culture plate leaving a gap of 0.3 cm between the edge of the insert and the edge of the well of the tissue culture plate. The well with transwell insert was incubated for up to 18 hours at 37° C. on the heated stage of a microscope and viewed by time lapse videomicroscopy recording at 120 frames per hour or by Polaroid still photography. Maintenance of a gradient was assessed by loading of methylene blue into the insert and observing a preserved gradient of color over the incubation period.

In the third semi-quantitative migration assay, T-cell subpopulations ($1 \times 10^5$ cells) were mixed with 0.5 ml of 0.5% methylcellulose (Stem Cell Technologies. Vancouver, BC) in sterile medium and plated in a 24 well plate. 5 μl of PBS or SDF-1α at concentrations of 10 μg/ml or 100 ng/ml was then dispensed gently into the methylcellulose at a set position on the edge of the well prior to incubation for up to 18 hours on a heated (37° C.) microscope stage and viewed by time lapse videomicroscopy.

Transmigration Assays: Use of Thymic Stromal-cell Medium(TSCM)

The chemotaxis assays used in this study were as for the SDF-1α described above. Quantitative chemotaxis transmigration assays were performed also using a transwell system. Serum free human fetal thymic stroma conditioned medium was added to the top, bottom or top and bottom chambers of the transwell in order to assess the chemotactic activities within the conditioned medium at dilutions of 1:2, 1:10 and 1:15 in serum free IMDM. Heat-inactivated TSCM was also used in the chemotaxis assay.

Cell migration was allowed to occur for 3 hours at 37° C. in an incubator (5% $CO_2$). Cells were harvested from the lower chamber after 3 hours and accurate cell counts, immunophenotypes, and chemokine receptor expression were determined for the cells which had emigrated from the upper chamber to the lower chamber.

Transmigration Assays: Use of SDF-1, Recombinant HIV-$1_{IIIB}$ gp 120 and Inhibitors Two chemotaxis assays were used in this study. First, quantitative chemotaxis transmigration assays were performed as for the SDF-1 described above (and Kim, et al., Blood, 1998, 91:4434). Purified T-cell and thymocyte subpopulations ($5 \times 10^4$ cells) were added to the upper chamber of each well in a total volume of 150 μl of IMDM alone. SDF-1α a (PeproTech, Rocky Hill, N.J.) was used at concentrations of 10 μg/ml, 1 μg/ml, 100 ng/ml, 10 ng/ml and 0 ng/ml in the lower, upper or both lower and upper chambers of the transwell to generate a checkerboard analysis matrix of positive, negative and absent gradients of SDF-1, respectively. Recombinant endotoxin free HIV-$1_{IIIB}$ gp 120 (Intracel, Rockville, Md.) was also utilized as a chemokinetic stimulus for peripheral blood T-cells at concentrations of 2 ng/ml, 20 ng/ml, 200 ng/ml and 2 μg/ml.

Cells were pretreated with anti-CXCR-4 (Pharmingen, San Diego, Calif.) at 20 μg/ml for 30 minutes at room temperature, pertussis toxin (PTX) (100 ng/ml for 1 hour at 37° C.). genistein (1 μg/ml for 20 minutes at 37° C.), herbimycin (1 μM for 20 minutes 37° C.), wortmannin (1 μM for 20 minutes at 37° C.), 8-Br-cAMP (100 μM for 15 minutes at room temperature) or 8-Br-cGMP (100 μM for 15 minutes at room temperature) (Sigma Chemical Company, St Louis, Mo.) prior to their addition to the upper chambers of the transwells in selected experiments. Transwells prepared in this way were incubated for 3 hours at 37° C./5% $CO_2$ incubator. Cells were harvested from the lower chamber after 3 hours and cell counts performed using a hemocytometer.

In the second semi-quantitative migration assay, T-cell subpopulations ($1 \times 10^5$ cells) were mixed with 0.5 ml of 0.5% methylcellulose (Stem Cell Technologies, Vancouver, BC) in sterile medium and plated in a 24 well plate. 5 μl of PBS or SDF-1α at concentrations of 10 μg/ml or 100 ng/ml, was then dispensed gently into 0.5 ml of methylcellulose at a set position on the edge of the well prior to incubation for up to 18 hours on a heated (37° C.) microscope stage and the movement of cells viewed by time lapse videomicroscopy.
Modulation of T-cell Infiltration Into the Site of a Secondary Immune Response by SDF-1 in vivo C57/B6 mice (Jackson Laboratories, Me.) were obtained and primed subcutaneously with 100 µg chicken ovalbumin (Sigma) containing less than 0.01% LPS by the limulus assay and dissolved in 100 µl of Complete Freund's Adjuvant (CFA) (Sigma). Three days ova-primed mice were challenged by intraperitoneal (IP) injection with 100 µg of ovalbumin (Ova) dissolved in 250 µl of ddH$_2$O. A second 250 µl IP injection was given to these mice the following day which contained murine SDF-1α at 100 ng/ml, 1 µg/ml or 5 µg/ml. These mice were then euthanized 24 hours following the second IP injection and peritoneal lavage with 5 mls of PBS performed with direct visualization of the peritoneal sac and its contents in order to avoid peripheral blood contamination. Peritoneal fluid cells harvested in this way contained<0.1% red blood cells. Three groups of control mice were used. In the first. C57/B6 mice were euthanized prior to Ova-priming and a peritoneal lavage performed. The second group of control mice were primed subcutaneously and challenged with Ova intraperitoneally as above and then euthanized 24 hours later. The third group were primed and challenged with Ova as above and after 24 hours injected intraperitoneally with 250 µl of ddH$_2$O alone. These mice were euthanized and a peritoneal lavage performed 24 hours later. Three independent experiments were performed with two or three mice in each experiment.

Cells harvested from the peritoneal fluid were counted with a hemocytometer and their viability determined by Trypan blue exclusion and the total viable nucleated cell count per ml of peritoneal fluid was determined. Peritoneal fluid harvested in this way was found to contain<0.1% red blood cells. Hematological smears of peritoneal fluid were also prepared and stained with Giemsa. Flow cytometry using a FacsCalibur flow cytometer (Becton Dickenson) was then performed on peritoneal fluid cells using two panels of anti-murine T-cell monocyte antibodies (anti CD3-PE, anti CD8-PERCP, anti CD4-APC and anti TCRγδ, anti-CD11b, anti TCRαβ) (Caltag) and isotype controls. The proportion of T-cells of each subpopulation (CD3$^+$, CD3$^+$CD4$^+$, CD3$^+$CD8$^+$) was determined as a percentage of the total nucleated cell fraction in the peritoneal fluid.

Results

SDF-1α is a chemokine produced by thymic and bone marrow stroma [12-15] which we evaluated for chemokinetic effects on subpopulations of human T cells, initially within circulating adult T cells and then fetal thymocytes and circulating T cells from the same fetus. Adult peripheral blood T-cells were isolated to a purity of ≧99% by flow cytometry into subpopulations of CD4$^+$CD45RA$^+$ and CD8$^+$CD45RA$^+$ (representing naïve cells) and CD4$^+$CD45RO$^+$ and CD8$^+$CD45RO$^+$ (representing memory cells). All populations were represented (15–31% of total lymphoid cells) and demonstrated high percentages of cells positive for the SDF-1α receptor, CXCR-4.

Using a standard transwell transmigration assay, SDF-1α demonstrated chemokinetic and chemoattractant activities for each subpopulation in relative order of CD8$^+$CD45RA$^+$>CD4$^+$CD45RA$^+$>CD4$^+$CD45RO$^+$>CD8$^+$ CD45RO$^+$. Peak chemoattractant activities were seen at a concentration of 100 ng/ml with 97% of CD8$^+$CD45RA$^+$, 85% of CD4$^+$CD45RA$^+$, 79% of CD4$^+$CD45RO$^+$ and 51% of CD8$^+$CD45RO$^+$ T-cells transmigrating in response to a positive gradient of SDF-1α.

Figure 1B:
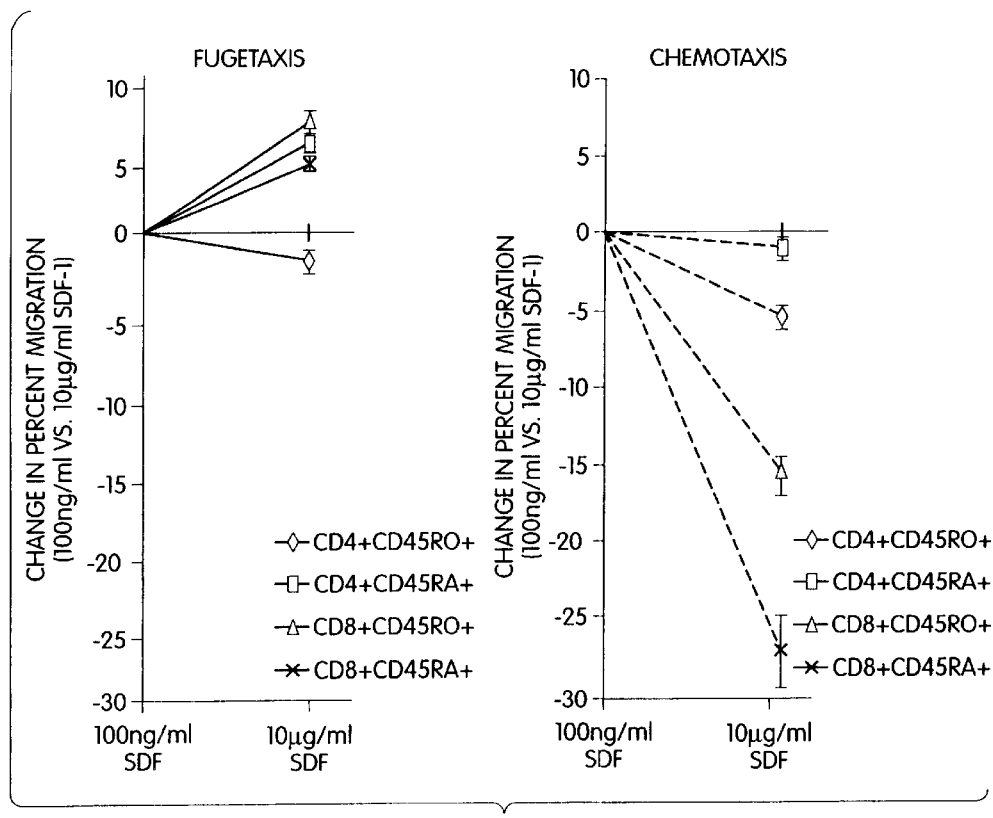
FIG. 1(B). Graphs showing the effects of various SDF-1α concentrations on T-cell subsets.

Increasing the SDF-1α a concentration to 1 µg/ml and 10 µg/ml diminished the proportion of cells responding toward a concentration gradient and initiated the movement of T-cells away from SDF-1α, a phenomenon we termed fugetaxis. Maximal fugetaxis was noted at 1 µg/ml for CD8$^+$CD45RO$^+$, CD8$^+$CD45RA$^+$ and CD4$^+$CD45RO$^+$ and at 10 µg/ml for CD4$^+$CD45RA$^+$ cells. The proportion of cells moving away from the SDF-1α at 10 µg/ml was in relative order CD8$^+$CD45RO$^+$~CD4$^+$CD45RA$^+$>CD8$^+$CD45RA$^+$>CD4$^+$CD45RO$^+$ and was significantly greater than chemokinesis for each subset of cells (p<0.01; Student t Test) (FIG. 1A). Movement of cells away from 10 µg/ml SDF-1α was consistently 2 to 10 times higher than chemokinesis and, for CD8$^+$CD45RA$^+$ and CD8$^+$CD45RO$^+$ cells, greater than chemotaxis. As the concentration of SDF-1α was increased from 100 ng/ml to 10 µg/ml, movement away from SDF-1α increased for all but CD4$^+$CD45RO$^+$ cells whereas chemotaxis toward SDF-1α a declined in all cells by up to a factor of 27-fold (FIG. 1B).

In order to further explore fugetaxis, a second cell migration assay was developed in which a tissue culture insert served as a reservoir of SDF-1α and was placed in the center of a tissue culture well containing dispersed cells in serum free medium. When the insert contained 10 µg/ml of SDF-1α, adult peripheral blood T-cell subpopulations in the tissue culture well were observed to migrate towards the source of SDF-1α and a second population to migrate away. Only movement toward the insert was seen when the insert contained SDF-1α at 100 ng/ml. The polarization of T-cell subpopulations both towards and away from SDF-1α was also not seen when serum free medium was applied to the insert or when high concentrations of SDF-1α existed in both the insert and surrounding medium in the tissue-culture well.

To further validate the process of concentration dependent directional movement, a third transmigration assay was used. T-cell subpopulations (1×10$^5$ cells) were plated in a semi-solid methylcellulose matrix, SDF-1α was loaded at a fixed position and cell trafficking was recorded by time lapse videomicroscopy. The movement of a gradient across the methylcellulose was documented in independent experiments by monitoring a dye front through the culture, a process not achieving equilibrium over the duration of our incubations. Consistent movement of peripheral T-cell subpopulations was seen away from high concentrations of SDF-1α and towards low concentrations SDF-1α.

To investigate whether the movement away from high concentrations may be relevant for egress of mature cells from sites of differentiation, we examined cells representing stages of T cell development from the thymus and peripheral blood from individual abortuses. Fetal blood CD4$^+$CD45RA$^+$ and CD8$^+$CD45RA$^+$ T-cell subpopulations showed levels of CXCR-4 expression comparable to the same immunophenotypic populations in adult peripheral blood. Triple negative (TN), double positive (DP) and single positive (SP) fetal thymocytes were less often CXCR-4 positive than either fetal or adult peripheral blood T-cells (p<0.05, Paired t Test). Mean fluorescent intensities of CXCR-4 on expressing thymocytes were also lower than on blood T-cells (p<0.01, Paired t TFest). Transmigration analysis of TN, DP and SP subpopulations of fetal thymocytes and CD4$^+$CD45RA$^+$ and CD8$^+$CD45RA$^+$ fetal blood T-cells demonstrated minimal cell movement in response to SDF-1α except in the most immature TN subset. In no thymocyte subpopulation was fugetaxis noted above background chemokinesis levels in response to SDF-1α, even at 1 µg/ml and 10 µg/ml.

Both $CD4^+CD45RA^+$ and $CD8^+CD45RA^+$ fetal blood T-cells showed significantly higher levels of chemotaxis and fugetaxis from SDF-1α than DP and SP thymocytes derived from the same fetuses ($p<0.05$; Paired t Test). As with adult peripheral blood T-cells, fetal blood T-cells demonstrated maximal chemotactic responses at concentrations of SDF-1α of 100 ng/ml whereas fugetaxis was seen at concentrations of SDF-1α between 1 μg and 10 μg/ml. Thus fetal samples from the same individual demonstrated the acquisition of fugetaxic ability only when T cells had exited the thymus into the circulation. The ability to undergo fugetaxis had marked differentiation stage specificity which was consistent with what we observed in the in vitro T cell differentiation system in which cells moved to the tissue culture well margins when fully differentiated.

Figure 2:
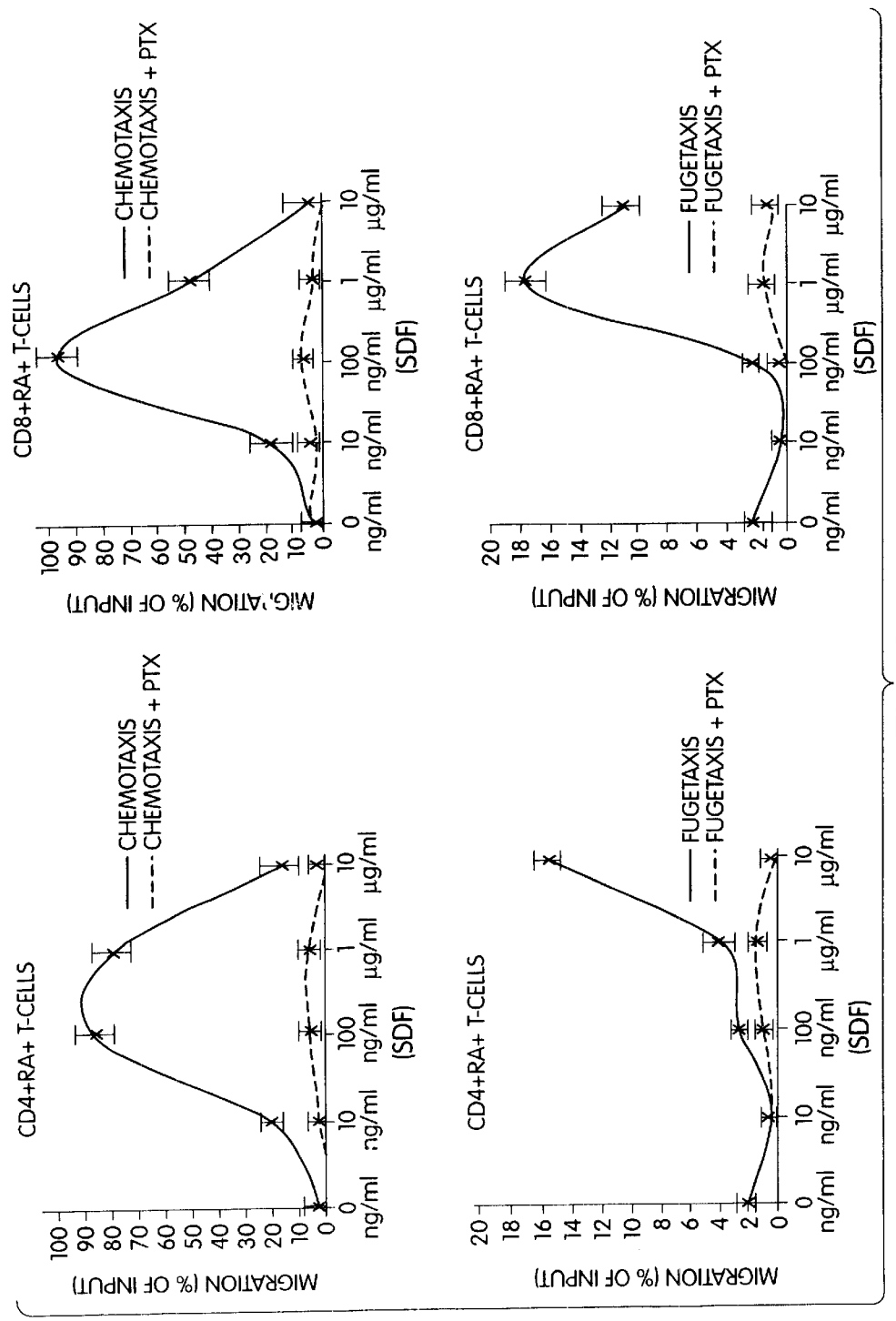
FIG. 2. Dose response curves to SDF-1α, showing that both fugetaxis and chemotaxis are inhibitable by pertussis toxin.

We next evaluated whether the processes of cell movement toward or away from a chemokine signal were similarly mediated. Pertussis toxin (PTX), which inhibits $G\alpha_i$ coupled signalling, inhibited all cell movement responses to SDF-1α at concentrations between 10 ng/ml to 10 μg/ml (FIG. 2). However, kinase inhibitor pre-incubation yielded distinct inhibition profiles for fugetaxis compared with chemotaxis. This was most readily seen with concentrations of SDF-1α that induced peak chemotaxis (100 ng/ml) or peak fugetaxis 10 μg/ml). The tyrosine kinase inhibitors, genistein and herbimycin, inhibited chemotaxis, but had minimal effect on fugetaxis. The PI-3 kinase inhibitor, wortmannin, comparably inhibited fugetaxis, chemotaxis and chemokinesis. This differential sensitivity to kinase inhibitors indicated unique signaling pathways mediating fugetaxis compared with chemotaxis to the same ligand.

Effects of TSCM (Thymic Stroma Conditioned Medium) on T-cell Transmigration

Figure 3:
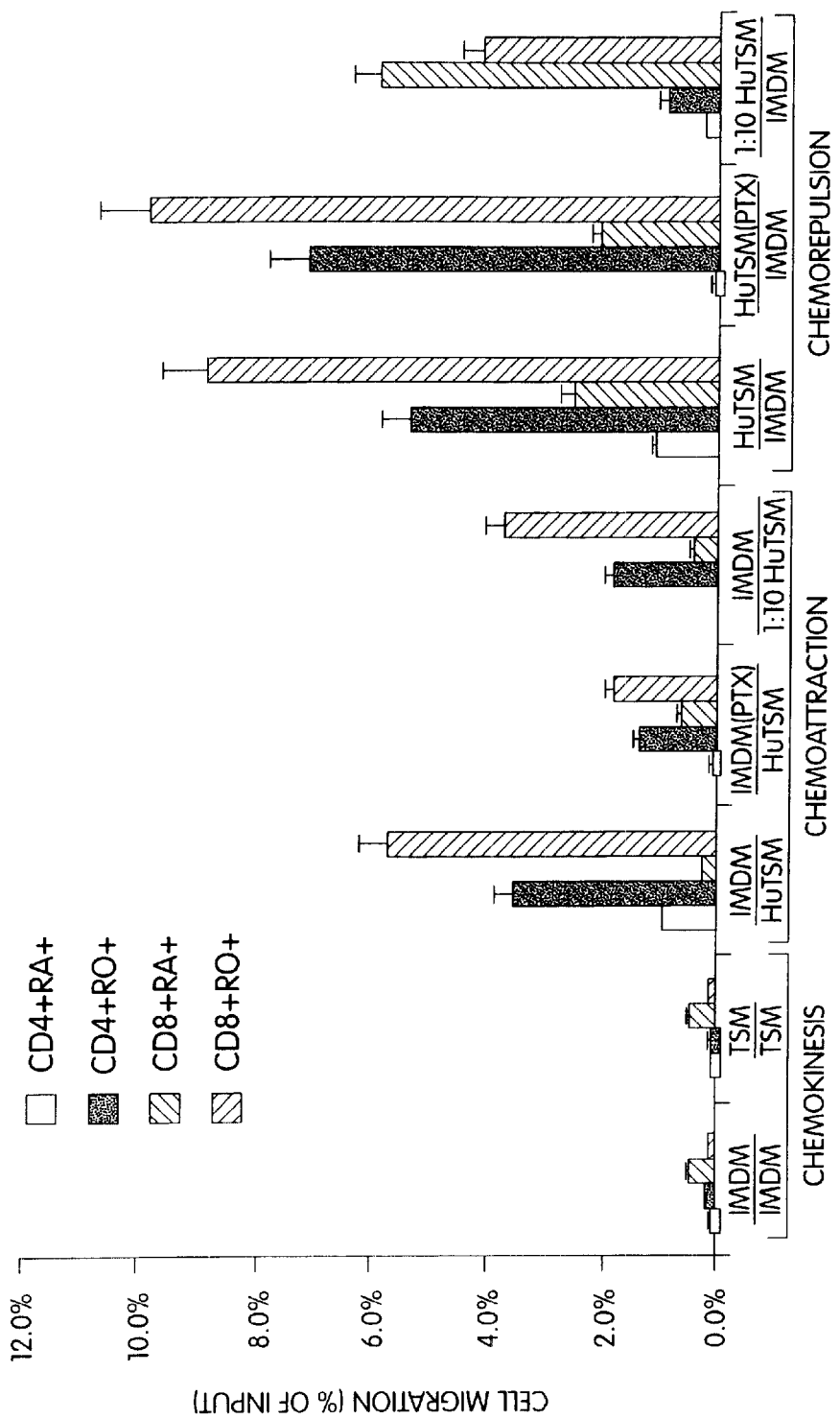
FIG. 3. Bar graph displaying the effect of human thymic stromal-cell isolate (TSCM) on peripheral blood T cell populations.

TSCM also demonstrated clear chemokinetic and chemoattractant activities for each of the four subpopulations of T-cells (see FIG. 3). The order of chemoattractant activity was CD8+CD45RO+>CD4+CD45RO+> CD4+CD45RA+ >CD8+ CD45RA+. The chemoattractant effect of TSCM could be diluted out and was inhibitable by PTX. TSCM had minimal chemokinetic activities on all the T-cell subpopulations studied. The movement of cells away from TSCM was also demonstrated in all the T-cell subpopulations studied. In CD8+CD45RO+ and CD4+CD45RO+ cell populations, this movement of cells away from TSCM was reduced by dilution of the TSCM dose. However, the TSCM was enhanced by dilution in the CD8+CD45RO+ T-cell population. SDF-1α and SDF-1β were not detectable by immunoassay at concentrations above 10 ng/ml in TSCM. Moreover, when fractionated, different fractions of TSCM had different effects on $CD4^+RO^+$ T cell transmigration. Chemoattractant activity resided with fraction 4 (pH 5.2. 0.25M NaCl) of the eluate, while fugetactic activity was associated with fraction 10 (pH 6.3. 0.5M NaCl) of the eluate.

The foregoing data demonstrate that subpopulations of human T-cells undergo purposeful movement away from high concentrations of SDF-1α and TSCM. The local concentrations of chemokines in tissue may be difficult to assess given the high affinity for proteoglycan binding, but has been postulated in the micromolar ranged[16] and some chemokine concentrations in biologic fluids have been calculated at>1 μg/ml. Our data suggest that SDF-1α and TSCM participate in the process of emigration of mature cells from the thymus and provide one explanation for the observation made 8 years ago that transgenic mice expressing pertussis toxin driven by the lck promoter, were capable of forming normal, fully differentiated T cells, but that these cells failed to make their exit from the thymus[1].

Fugetaxis is CXCR-4 Mediated

We next evaluated whether the processes of cell movement toward or away from a chempkine signal were mediated via similar signal transduction pathways. Pre-incubation of cells with an anti-CXCR-4 specific monoclonal antibody that inhibits SDF-1 signaling resulted in inhibition of both chemotaxis and fugetaxis of T-cell subpopulations in response to concentrations of SDF-1α varying between 10 ng/ml and 1 μg/ml. In addition, PTX, which inhibits $G\alpha_i$ signaling, inhibited T-cell movement toward and away from SDF-1α at concentrations between 10 ng/ml and 10 μg/ml. Pre-incubation of cells with kinase inhibitors, however, resulted in distinct inhibition profiles for fugetaxis compared with chemotaxis. This was most readily apparent with SDF-1α concentrations that induced peak chemotaxis (100 ng/ml) or peak fugetaxis (1 μg/ml or 10 μg/ml).

Chemokines, including SDF-1, have been shown to activate multiple signal transduction pathways including phosphatidylinositol 3-kinase (PI-3) and tyrosine kinase (Ganju, et al., *J. Biol. Chem.*, 1998, 36, 23169; Turner, et al., *J. Immunol.* 1995, 5:2437; Turner, et al., *J. Biochem. Soc. Trans.*, 1977, 2:216S). We postulated that the signals for fugetaxis or chemotaxis may have differential sensitivity to PI-3 and tyrosine kinase inhibitors. The PI-3 kinase inhibitor, wortmannin, comparably inhibited fugetaxis, chemotaxis and chemokinesis induced by SDF-1. In marked contrast, the tyrosine kinase inhibitors genistein and herbimycin inhibited chemotaxis, but had minimal effect on fugetaxis. Cyclic nucleotides serve as signaling intermediates for multiple G-protein coupled receptors (Daaka, et al., *Nature*, 1997, 6655, p88; Selbie, et al., *Trends Pharmacol Sci*, 1998, 3:87–93) and have been shown to convert neuronal growth cone responses to netrin-1 from repulsion to attraction (Song H-J, et al., *Science*, 1998, 281:1515). We noted that the membrane-permeable cAMP agonist, 8-Br-cAMP inhibited fugetaxis but not chemotaxis, and that inhibition was concentration dependent. Taken together, these data suggest that fugetaxis and chemotaxis result from the differential activation of signal transduction pathways in response to different concentrations of the same ligand.

HIV-$1_{IIIB}$ gp120 is a Bidirectional Cue for T-cell Migration in vitro

To further confirm the role of CXCR-4 in mediating the fugetaxis signal, we used purified endotoxin free HIV-$1_{IIIB}$ gp120 (also known as X4-HIV-1 gp120) on $CD8^+$ $CD45RA^+$ T-cells (a subpopulation of human resting peripheral blood T-cells). SDF-1 independent and CD4 independent, chemotaxis and fugetaxis were observed in a concentration dependent manner (FIG. 4), however, the proportion of cells undergoing chemotaxis was substantially less than that seen with SDF-1. High concentrations of HIV-$1_{IIIB}$ gp120 (2 μg/ml) caused maximal migration of T-cells away from the HIV protein. In contrast, peak concentrations of HIV-1 gp120 of about 200 ng/ml caused T-cells to move towards the recombinant retroviral protein. Similar to SDF-1, the bidirectional movement of T-cells induced by HIV-$1_{IIIB}$ gp120 was inhibited by pertussis toxin and the PI-3 kinase inhibitor wortmannin. In addition, movement away from HIV-$1_{IIIB}$ gp120 was differentially sensitive to inhibition by the cAMP agonist, 8-Br-cAMP. Furthermore, HIV-1 specific CTL clones derived from HIV-infected patients were shown to exhibit a bidirectional response to X4-HIV-1 gp120.

We conclude, therefore, that CXCR-4 ligands that include but are not limited to, SDF-1α and β, met-SDF-1β, HIV-$1_{IIIB}$ gp120, small molecules T134 and MD3100, T22 [Tyr5, 12,Lys7]-polyphemusin II, agonists for such molecules, and the like, have a concentration dependent bifunctional effect on the migration of subpopulations of human T-cells.

SDF-1 Concentrations in vivo Alter Inflammatory Infiltrates

Figure 5:
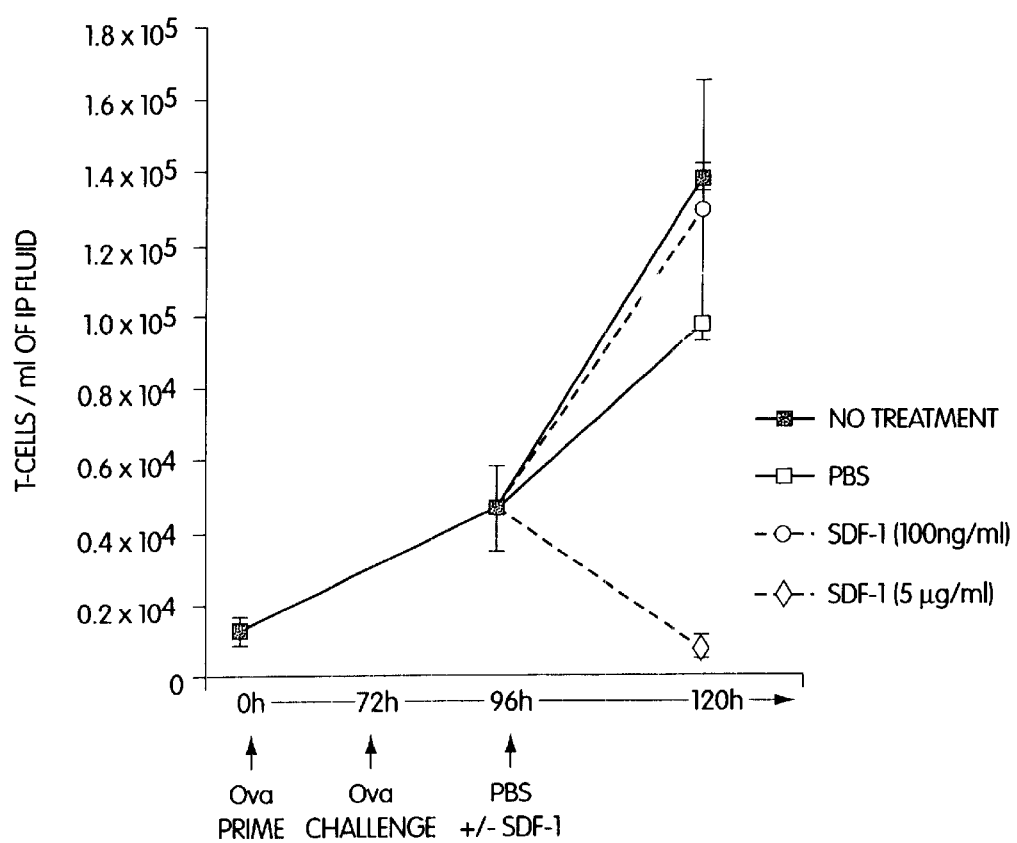
FIG. 5. Graphs depicting that SDF-1 at high concentration (5 µg/ml), causes T cell migration away from a site of secondary immune response in vivo.

To evaluate whether the phenomenon of T cell movement away from high concentrations of SDF-1 was relevant to in vivo immune physiology, we immunized and subsequently challenged C57BL/6 mice with ovalbumin. We selected intraperitoneal challenge due to our ability to recover cells efficiently in quantities sufficient for flow cytometric analysis. Twenty-four hours following the challenge dose of Ova we injected mice with equivolume amounts of PBS, or low or high concentrations of SDF-1. After an additional 24 hours, Ova-challenged animals that had either not been injected or injected with PBS or SDF-1 were sacrificed and cells at the site of challenge quantitated and immunophenotyped. No significant differences in T cell accumulation were noted between those animals that were either sham injected, injected with PBS, or injected with SDF-1 at low dose (100 ng/ml) and all demonstrated marked T cell infiltration above that of baseline or 24 hours post antigenic challenge. In marked contrast, T cell infiltration with high dose SDI-1 (5 µg/ml) was blunted significantly below that of controls (p=0.02) demonstrating the ability of high concentrations of a chemokine to mitigate and perhaps, reverse the potential of T cell accumulation at sites of inflammation. Of note, the concentrations of SDF-1 used had no demonstrable toxicity on T cells of the four subsets used in the in vitro analyses and no evidence of apoptosis on murine PBMC or $CD3^+$ cells. (See FIG. 5).

Purification of Putative Fugetaxins Derived from Cancer Cell Lines

Preparation of HepG2 Conditioned Medium (HepG2CM)

The HepG2 cell line (derived from a human hepatocarcinoma—ATCC no:HB-8065, ATCC, Manassas, Va.) was grown to confluency in MEM+10% heat inactivated fetal calf serum+penicillin/streptomycin+L-glutamine. Confluent HepG2 cells were then transferred into serum free medium for 48 hours and the serum free conditioned medium (HepG2CM) was harvested from these cultures. HepG2CM was filtered through a 0.4 µm filter prior to use in transmigration assays or in the Fugetaxin separation system detailed below.

Preparation of Fractions of HepG2 CM Containing a Putative Fugetcixin

1. Heparin is a highly sulfated glycosaminoglycan with the ability to bind most glycosylated secreted protein specifically. 200 ml of HepG2CM were loaded onto a 5-ml HiTrap heparin column (Pharmacia) equilibrated with 10 mM Na phosphate, pH 7. The column was eluted with step increasing concentration of NaCl. Major fugetactic activity was detected in the 0.3M NaCl eluted fraction (active fraction).
2. A cation exchange column, HiTrap Sp Sepharose (Pharmacia), was used as a second step of purification. The active fraction from the Heparin column was dialysized against 50 mM MES, pH6.4 and loaded onto a 1-ml HiTrap Sp column equilibrated with 50 mM MES, pH6.4. The column was then eluted with a linear gradient of NaCl concentration.
3. MonoQ is an anion exchanger with unique hydrophilic polymer particles designed for fast and high-resolution separation of proteins. The active fraction eluted from the HiTrap Sp column in the previous step was then dialysized with 20 mM Tris, pH8.0 and further fractionated using a MonoQ HR5/5 column (Pharmacia). The column was then eluted with a linear gradient of NaCl concentration. By comparing fugetactic activity profile (using a standard transmigration assay) and a silver-stained SDS-PAGE gel, a particular band at approximately 110 kDa (p110) in fraction#18 was found always to correlate with such fugetactic activity.
4. Microsequencing of p110: To identify p110 candidate, MALDI-TOF MS (matrix-assisted laser desorption/ionization and time-of flight mass spectrometer) of tryptic digestion products were performed. The resulted peptide masses were used to search protein and DNA sequence database with an enhanced version of the FRAGFIT program (Henzel W J, 1993, pnas 90, 5011 and Arnott D, 1998, Electrophoresis 19, 968). Mass spectrometer results indicated that p110 is the protein previous identified as inter-α-trypsin inhibitor heavy-chain II precursor (ITI H2). ITI H2 is a member of inter-α-trypsin inhibitor (ITI) family, which consist of a group of plasma proteins synthesized in the liver. Human ITI H2 is a glycoprotein composed of 946 amino acids (including a signal peptide of 18 aa) (SEQ ID NO: 1). It can undergo N-terminus and C-terminus cleavage steps after its secretion into plasma, eventually resulting in a 648 aa mature protein. ITI proteins, which is built up from heavy (H1, H2, H3, H4) and light (bikunin) chains, and belongs to the superfamily of Kunitz-type protease inhibitors. Bikunin with a double-headed kunitz-type protease inhibitor sequence is the reason for the serine protease inhibitor activity. However, the array of proteases that are inhibited by ITI family members in vitro are more efficiently inhibited by other protease inhibitors in plasma. Therefore, the biological significance of ITI family members as protease inhibitors is unknown (Salier J P, Trends Biochem. Sci., 1990, 15:435). It has been suggested that ITI family members are involved in extracellular matrix stabilization (Chen L. et al., J. Biol. Chem., 1994, 269:28282), tumor invasion (Kobayashi H. et al., J. Biol. Chem., 1995, 270:8361), metastasis (Kobayashi H. et al., Int. J. Cancer, 1995, 63:455) and arthritis (Hutadilok N. et al., Ann. Rheum. Dis., 1988, 47:377).

Biological Activity of Fraction 18 of HepG2CM in vitro and in vivo

Fraction 18 at a 1:10 dilution in serum free medium (original fraction volume between 100–200 µl), was consistently shown to contain maximal fugetactic activity for Jurkat T-cells as described above. We examined the biology of the fugetactic activity of Fraction 18 with in vitro and in vivo transmigration assay systems.

Inhibitor Sensitivity of Fraction 18 in vitro

Jurkat T-cells were pretreated with anti-CXCR-4 (Pharmingen) (at 20 µg/ml for 30 minutes at room temperature), pertussis toxin (PTX) (100 ng/ml for 30 minutes at 37° C.), genistein (1 µg/ml for 20 minutes at 37° C.), herbimycin (1 µM for 20 minutes 37° C.), wortmannin (1 µM for 20 minutes at 37° C.), 8-Br-cAMP (100 µM for 15 minutes at room temperature) or 8-Br-cGMP (100 µM for 15 minutes at room temperature) (Sigma Chemical Company, St Louis, Mo.), prior to their addition to the upper chambers of the transwells in selected experiments. Transwells prepared in this way were incubated for 3 hours at 37° C./5% $CO_2$ incubator. Cells were harvested from the lower chamber after 3 hours and cell counts performed. The effect of inhibitors on transmigration of Jurkat cell migration was examined. CXCR-4, genistein and herbamycin inhbited fugetaxis induced by Fraction 18 to 40–60% of the control level. PTX inhbited fugetaxis in response to Fraction 18 to 30% of the control level. The cAMP agonist, 8-Br-cAMP, resulted in 95% inhbition of fugetaxis whereas 8-Br-cGMP did not significantly inhbit fugetaxis.

Activity of Fraction 18 in vivo

C57 BL/6J mice (Jackson Laboratories, Bar Harbor, Me.) were primed subcutaneously with 100 kg chicken ovalbumin (Ova) (Sigma) containing less than 0.01% LPS by the limulus assay and dissolved in 100 µl of Complete Freund's Adjuvant (CFA) (Sigma). Three days later Ova-primed mice were challenged by intraperitoneal (IP) injection with 100 µg of Ova dissolved in 250 µl of ddH$_2$O. A second 250 µl IP injection was given to these mice the following day, which contained a 1:10 dilution of HepG2 CM fraction 18, fraction 22 (without significant fugetactic activity in vitro) or column pass through (PT). These mice were euthanized 3 and 24 hours following the second IP injection and peritoneal lavage with 5 mls of PBS performed with direct visualization of the peritoneal sac and its contents in order to avoid peripheral blood contamination. Peritoneal fluid cells harvested in this way contained <0.1% red blood cells.

Three groups of control mice were used. In the first, C57 BL/6J mice were euthanized prior to Ova priming and a peritoneal lavage performed. The second group of control mice were primed subcutaneously and challenged with Ova intraperitoneally as above and then euthanized 3 and 24 hours later. The third group were primed and challenged with Ova as above and injected intraperitoneally with 250 µl of ddH$_2$O alone 24 hours later. These mice were euthanized and a peritoneal lavage performed after a further 3 and 24 hours. Three independent experiments were performed with two or three mice in each group in each experiment.

Cells harvested from the peritoneal fluid were counted with a hemocytometer and their viability determined by trypan blue exclusion and the total viable nucleated cell count per ml of peritoneal fluid was determined. Peritoneal fluid harvested in this way was found to contain <0.1% red blood cells. Hematological smears of peritoneal fluid were also prepared and stained with Giemsa. Flow cytometry using a FACSCalibur flow cytometer (Becton Dickinson) was then performed on peritoneal fluid cells using two panels of anti-murine T-cell and monocyte antibodies (anti CD3-PE, anti CD8-Biotin, anti CD4-APC and anti TCRγδ, anti-CD11b, anti TCR αβ-FITC) (Caltag Laboratories, San Francisco, Calif.) and isotype controls (Caltag). Second-step staining of biotin-conjugated antibodies was performed using streptavidin-PERCP (Becton Dickinson). The proportion of T-cells of each subpopulation (CD3$^+$, CD3$^+$CD4$^+$, CD3$^+$CD8$^+$) was determined as a percentage of the total nucleated cell fraction in the peritoneal fluid.

Figure 6:
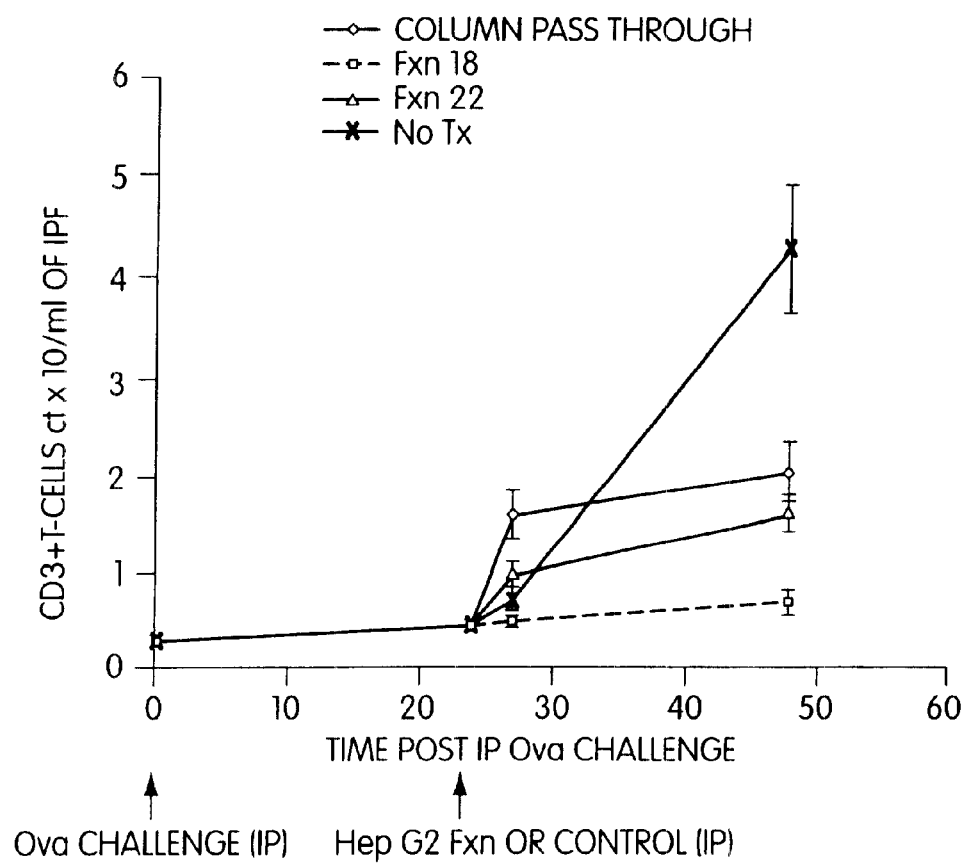
FIG. 6. Graph depicting that HepG2CM Fraction 18 abrogates T-cell infiltration to a site of antigenic challenge in vivo.

Fraction 18 was shown to abrogate the T-cell infiltrate induced by IP challenge with Ova. Fraction 22 or pass through did not significantly effect T-cell emigration from the site of antigen challenge (FIG. 6).

According to this aspect of the invention, other members of the inter-α-trypsin inhibitor heavy-chain II precursor (ITI H2) family of polypeptides are believed to have similar fugetactic activity, and are therefore useful according to the invention. Such members include the polypeptides having sequences with GenBank Acc. Nos.: IYHU2, NP_034712, NP_002207, Q61703, P97279, O02668, CAA72308 (Y11545), BAA13939 (D89286), S54354, CAA49842 (X70392), AAA60558(M18193), CAA30160(X07173), 1409219A, and/or AAA59195(M33033).

Kaposi's Sarcoma Herpes Virus and Fugetaxis

The human Kaposi's sarcoma herpes virus (KSHV) causes a number of different neoplastic disorders in an immunocompromised host including Kaposi's Sarcoma. KSHV has been shown to encode a number of human chemokine homologues including vMIP I and vMIP-II which are homologous to the human chemokines MIP-1α and MIP-1β. We postulate that the viral chemokines exert a fugetactic response on human T-cells thereby allowing the tumor to escape immune control.

We examined the chemotactic and fugetactic responses of human T-cell subpopulations and KSHV specific CTL clones to the KSHV proteins vMIP-I and vMIP-II and serum free supernatants from two cell-lines well known in the art that are chronically infected by KSHV and derived from human tumors, lines BCBL-1 and VG-1. BCBL-1 is a B cell line derived from a body cavity-based B lymphoma that is latently infected with HHV-8/KSHV; no EBV DNA is present in this line (Renne, R., W. et al., *Nat. Med.*, 1996, 2:342–346).

Results

Significant fugetactic responses were discovered for CD4RA and CD4RO cells to VG-1 supernatants at a 1:2 dilution in serum free medium. and for CD4RO and CD8RO T-cells to BCBL-1 supernatant at a 1:2 dilution.

T-cell subsets also show a clear chemotactic response to MIP-1α at a concentration of 10 ng/ml. Of note, T-cells demonstrated a clear fugetactic response to vMIP-I but not vMIP-II at a concentration of 100 ng/ml.

BIBLIOGRAPHY

1. Chaffin K E and Perlmutter R M. A pertussis toxin-sensitive process controls thymocyte emigration. *Eur. J. Immunol.* 21: 2565–2573 (1991)
2. Craddock C F, Nakamoto B, Andrews R G, Priestley G V and Papayannopoulou T Antibodies to VLA4 integrin mobilize long-term repopulating cells and augment cytokine-induced mobilization in primates and mice. *Blood* 90, 4779–4788 (1997)
3. Doetsch R N and Seymour W F. Negative chemotaxis in bacteria. *Life Sciences* 9:1029–1037 (1970)
4. Bailey G B, Leitch G J and Day D B. Chemotaxis by entamoeba histolytica. *J Protozool* 32:341–346 (1985)
5. Tsang N, Mcnab R and Koshland D E Jr. Common mechanism for repellents and attractants in bacterial chemotaxis. *Science* 181:60–69 (1973)
6. Repaske D and Adler J. Change in intracellular pH of *Escherischia coli* mediates the chemotactic response to certain attractants and repellents. *J Bacteriol* 145:1196–1208 (1981)
7. Tisa L S and Adler J. Cytoplasmic free-Ca2+ level rises with repellents and falls with attractants in *Escherischia coli* chemotaxis. *Proc Natl Aca Sci U.S.A.* 92:10777–10781 (1995)
8. Taylor B L and Johnson M S. Rewiring a receptor: negative output from positive input. *FEBS Lett* 425:377–381 (1998)
9. Wells T N, Power C A and Proudfoot A E. Definition, function and pathophysiological significance of chemokine receptors. *Trends Pharmacol Sci* 19:376–380 (1998)
10. Luster A D. Chemokines—chemotactic cytokines that mediate inflammation. *N Engl J Med* 338:436–445 (1998)
11. Baggiolini M. Chemokines and leukocyte traffic. *Nature* 392:565–568 (1998)
12. Bleul C C, Fuhlbrigge R C, Casasnovas J M, Aiuiti A and Springer T A. A highly efficacious lymphocyte chemoattractant, stromal cell-derived factor 1 (SDF-1). J Exp Med 184: 1101–1109 (1996)
13. Kim C H, Pelus L M, White J R and Broxmeyer H E. Differential chemotactic behavior of developing T-cells in response to thymic chemokines. *Blood.* 91: 4434–4443 (1998)
14. Tashiro K, Tada H, Heilker R, Shirozu M, Nakano T and Honjo F. Signal sequence trap: cloning strategy for secreted proteins and type 1 membrane proteins. *Science,* 261: 600–603

15. Shirozu M, Nakano T, Inazawa J, Tashiro K, Tado H, Shinohara T and Honjo T. Structure and chromosomal localization of the human stromal cell-derived factor 1 (SDF1) gene. *Genomics* 28:495–500 (1995)
16. Bacon K B, Premack B A, Gardner P and Schall T J. Activation of dual T cell signaling pathways by the chemokine RANTES. *Science,* 269:1727–30 (1995)
17. Noble P B and Bentley K C. Locomotory characteristics of human lymphocytes undergoing negative chemotaxis to oral carcinomas. *Exp Cell Res* 133; 457–461 (1981)

DETAILED DESCRIPTION OF THE DRAWINGS

FIG. 1. SDF-1α induces fugetaxis, chemotaxis and chemokinesis that varies with input chemokine concentration. (A) Fugetactic (solid bars), chemotactic (striped bars) and chemokinetic (stippled bars) transmigration responses are shown in response to 10 μg/ml of SDF-1α for each of the four adult peripheral blood T-cell subpopulations (CD8$^+$CD45RO$^+$, CD4$^+$CD45RA$^+$, CD8$^+$CD45RO$^+$ and CD8$^+$CD45RA$^+$). Each data point represents the mean and S.E.M. of three independent experiments. (B) Depicts the percent change in fugetaxis and chemotaxis seen for the four adult peripheral blood subpopulations migrating in response to concentrations of SDF-1α between 100 ng/ml and 10 μg/ml.

FIG. 2. Both fugetaxis and chemotaxis are inhibitable by pertussis toxin. Dose response curves to SDF-1α are shown for fugetaxis and chemotaxis and individually for each of two adult peripheral blood T-cell subpopulations (CD4$^+$CD45RA$^+$ and CD8$^+$ CD45RA$^+$) without (—x—) and with (——x——) pretreatment with PTX. Each data point represents the mean and S.E.M. of three independent experiments.

FIG. 3. Chemotactic responses of peripheral bloodT cell subpopulations to Thymic Stroma Cell Medium (TSCM) Chemotaxis of purified T-cell subpopulations was examined in the transmigration system described above. In order to test positive chemotaxis or chemoattraction to TSCM. TSCM was placed at varying concentrations in IMDM in the lower chamber alone. To test for fugetaxis, TSCM was placed in the upper chamber to test for chemokinesis TSCM was placed in the upper and lower chambers. Chemokinesis was examined for cells treated with undiluted TSCM, TSCM diluted to 1:10, heat inactivated TSCM (preincubated at 65° C. for 60 minutes and TSCM in the context of cells pretreated with PTX. Chemotactic responses are shown for each of the three types of cell movement and individually for each of the four T-cell subpopulations (CD8$^{CD}$45RO$^+$, CD4$^+$CD45RA$^+$, CD8$^+$CD45RO$^+$ $^{and\ CD}$8$^+$CD45RA$^+$).

Figure 4A:
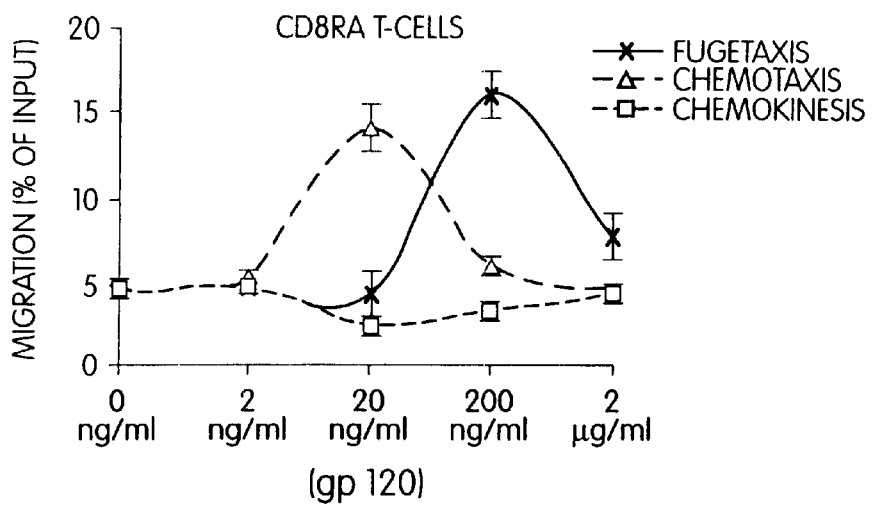
FIG. 4. Graphs showing that CD8$^+$CD45RA$^+$ T-cells fugetax in a CD4-independent, CXCR-4 dependent (FIG. 12B), concentration dependent manner (FIGS. 12A and 12C) in response to recombinant HIV-1$_{IIIB}$ gp120.
Figure 4B:
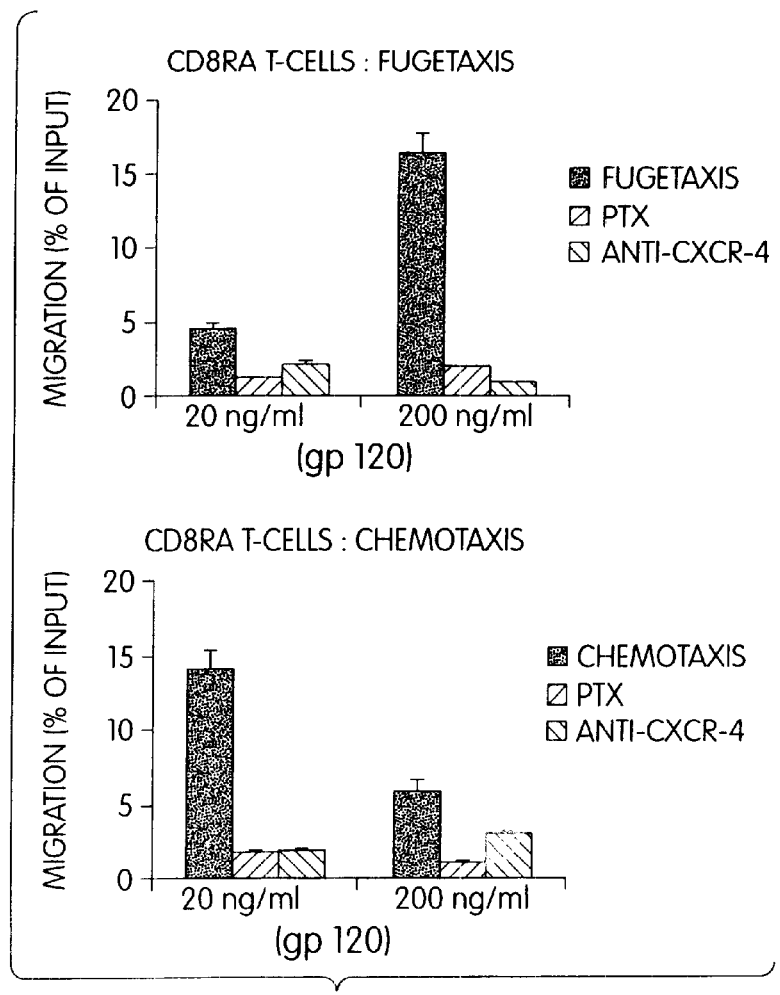
Figure 4C:
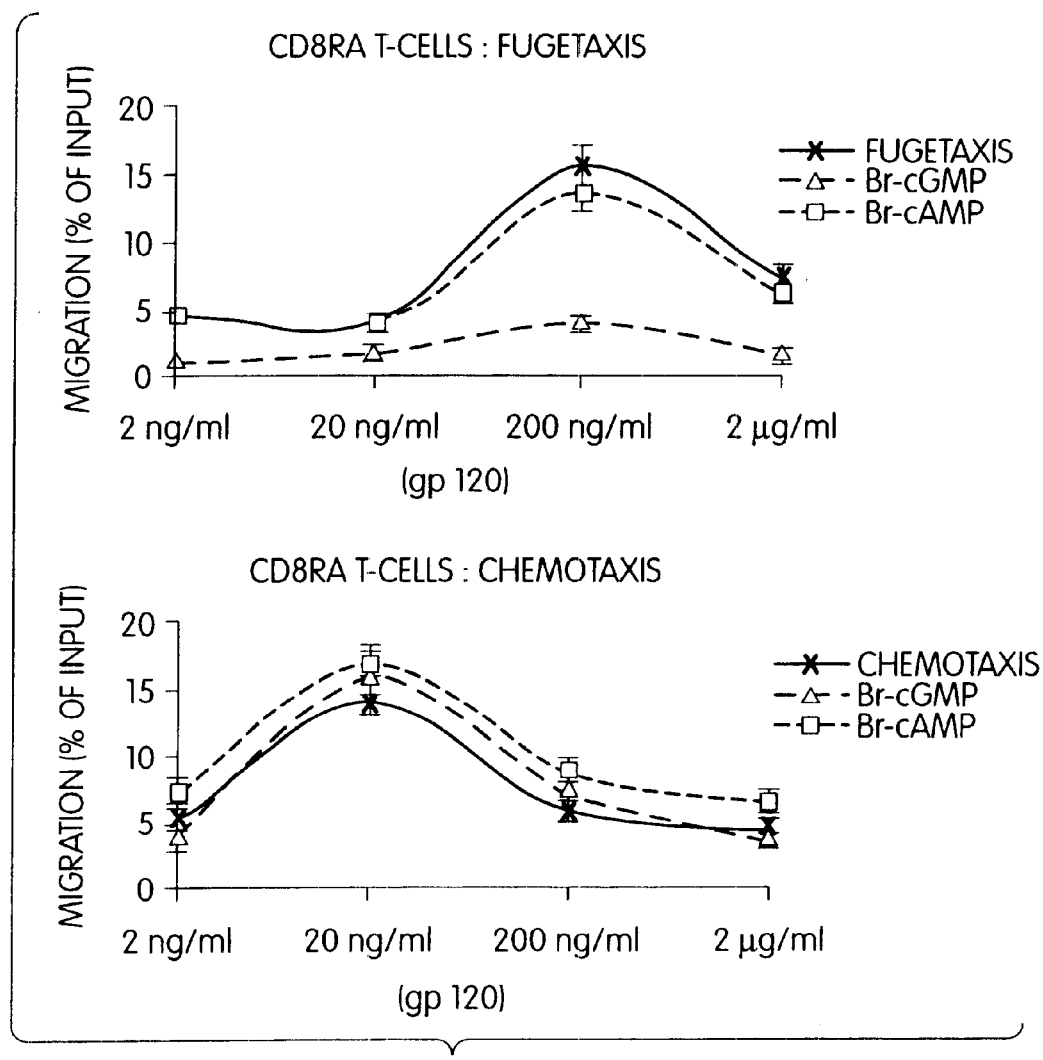

FIG. 4: CD8$^+$CD45RA$^+$ T-cells fugetax in a CD4-independent, CXCR-4 dependent, concentration dependent manner in response to recombinant HIV-1$_{IIIB}$, gp120. The concentration dependent chemotactic (————Δ————), fugetactic (—x—) and chemokinetic responses (————□————) of CD8$^+$CD45RA$^+$ T-cells to HIV-1$_{IIIB}$ gp120 was studied (FIG. 4A). Migratory responses of to CD8$^+$CD45RA$^+$ T-cells to HIV-1$_{IIIB}$ gp120 are shown following pretreatment of with anti-CXCR-4 (speckled bars), PTX (striped bars) and incubation in medium alone (solid bars) in response to concentrations of 20 ng/ml and 200 ng/ml of the recombinant HIV-1 glycoprotein (FIG. 4B). Of note, no fugetaxis of CD8$^+$CD45RA$^+$ peripheral blood T-cells was seen in response to the CCR-5 specific gp 120 derived from HIV-1 cm 235 (National Institutes of Health AIDS Reagent and Reference Program). CD8$^+$CD45RA$^+$ peripheral blood T-cells were incubated with the membrane permeable cyclic nucleotide inhibitors 8-Br-cAMP (————Δ————), 8-Br-cGML (————□————) or in medium alone (—x—) prior to there use in transmigration assays with varying concentrations of HIV-1 gp120. The concentration dependent chemotactic and fugetactic responses of the T-cells are shown (FIG. 4C). Each data point represents the mean and S.E.M. of three independent experiments.

Figure 7A:
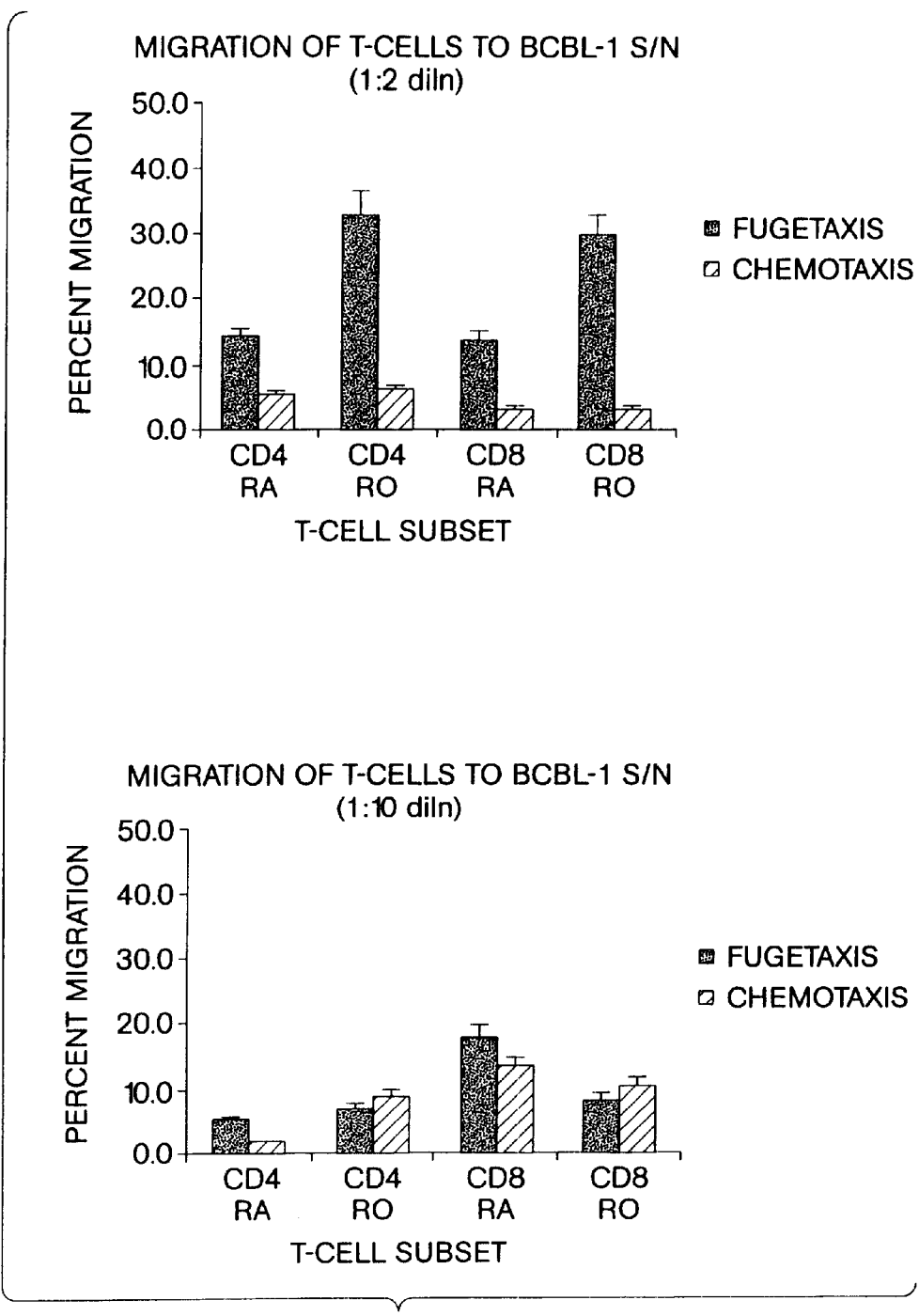
FIG. 7. Graphs showing that T-cell subsets fugetax in response to KSHV-infected cell-isolates (supernatants); (A) BCBL-1 cells; (B) VG-1 cells.
Figure 7B:
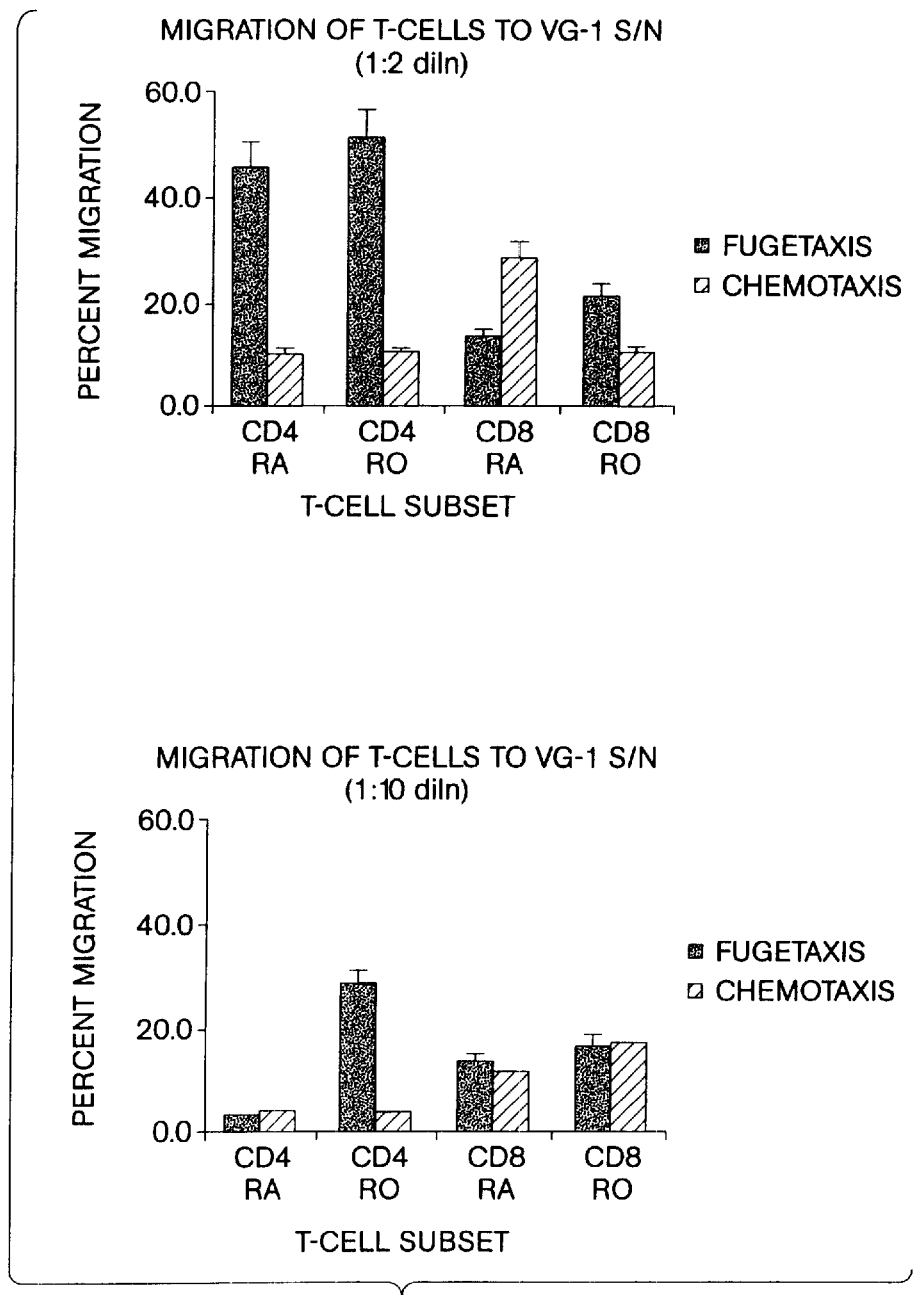

FIG. 7: Transmigration of human T-cells to supernatants derived from cell lines which are chronically infected with KSHV (FIG. 7A: BCBL-1, and FIG. 7B:VG-1). Fugetactic (black bars) and chemotactic (striped bars) migratory responses are shown. Significant fugetactic responses are shown for CD4RA and CD4RO cells to VG-1 supernatants at a 1:2 dilution in serum free medium and for CD4RO and CD8RO T-cells to BCBL-1 supernatant at a 1:2 dilution.

Equivalents

Those skilled in the art will recognize, or be able to ascertain using no more than routine experimentation, many equivalents to the specific embodiments of the invention described herein. Such equivalents are intended to be encompassed by the following claims. All references disclosed herein are incorporated by reference in their entirety.

What is claimed is presented below and is followed by a sequence listing.

We claim:

1. A method of repelling immune cells from a specific site in a subject, comprising:
    locally administering to a specific site in a subject in need of such treatment a fugetactic agent in an amount effective to repel immune cells from the specific site in the subject.

2. The method of claim 1, wherein the specific site is a site of inflammation.

3. The method of claim 2, further comprising co-administering a non-fugetactic agent that inhibits migration of immune cells to the site of inflammation in the subject.

4. The method of claim 3, wherein the non-fugetactic agent is an antiinflammatory agent.

5. The method of claim 1, wherein the subject has an autoimmune disease.

6. The method of claim 5, wherein the autoimmune disease is rheumatoid arthritis, uveitis, insulin-dependent diabetes mellitus, hemolytic anemias, rheumatic fever, Crohn's disease, Guillain-Barre syndrome, psoriasis, thyroiditis, Graves' disease, myasthenia gravis, glomerulonephritis, autoimmune hepatitis, or systemic lupus erythematosus.

7. The method of claim 1, wherein the subject has an abscess, a transplant, an implant, atherosclerosis, or myocarditis.

8. The method according to claim 1, wherein the fugetactic agent is SDF-1α at a concentration higher than about 1 μg/ml, non-diluted thymic stromal-cell-derived medium, concentrated thymic stromal-cell-derived medium, or a thymic stromal-cell-derived polypeptide factor.

9. The method of claim 8, wherein the thymic stromal-cell-derived polypeptide factor mediates its repellent effects through a G-protein transduction pathway.

10. The method of claim 9, wherein the thymic stromal-cell-derived polypeptide factor is not genistein inhibited.

11. The method of claim 9, wherein the thymic stromal-cell-derived polypeptide factor is wortmannin inhibited.

* * * * *